(12) United States Patent
Chey et al.

(10) Patent No.: US 11,000,474 B2
(45) Date of Patent: *May 11, 2021

(54) MICROCHIP SUBSTANCE DELIVERY DEVICES

(71) Applicant: International Business Machines Corporation, Armonk, NY (US)

(72) Inventors: S. Jay Chey, Hartsdale, NY (US); Bing Dang, Chappaqua, NY (US); John U. Knickerbocker, Monroe, NY (US); Kenneth F. Latzko, Carmel, NY (US); Joana Sofia Branquinho Teresa Maria, NY, NY (US); Lavanya Turlapati, White Plains, NY (US); Bucknell C. Webb, Ossining, NY (US); Steven L. Wright, Cortland Manor, NY (US)

(73) Assignee: International Business Machines Corporation, Armonk, NY (US)

( * ) Notice: Subject to any disclaimer, the term of this patent is extended or adjusted under 35 U.S.C. 154(b) by 359 days.

This patent is subject to a terminal disclaimer.

(21) Appl. No.: 15/852,943

(22) Filed: Dec. 22, 2017

(65) Prior Publication Data

US 2018/0133152 A1 May 17, 2018

Related U.S. Application Data

(63) Continuation of application No. 14/483,278, filed on Sep. 11, 2014, now Pat. No. 9,937,124.

(51) Int. Cl.
*A61M 31/00* (2006.01)
*A61N 1/04* (2006.01)
*A61K 9/00* (2006.01)

(52) U.S. Cl.
CPC .......... *A61K 9/0097* (2013.01); *A61N 1/0412* (2013.01); *A61M 31/002* (2013.01);
(Continued)

(58) Field of Classification Search
CPC .............. A61K 9/0097; A61M 31/002; A61M 2205/0244; A61N 1/0412; A61N 1/0428; A61N 1/0444; A61N 1/0448
(Continued)

(56) References Cited

U.S. PATENT DOCUMENTS

| 3,993,071 A | 11/1976 | Higuchi et al. |
| 4,917,895 A | 4/1990 | Lee et al. |

(Continued)

FOREIGN PATENT DOCUMENTS

| CN | 201725352 U | 1/2011 |
| CN | 202600746 U | 12/2012 |

(Continued)

OTHER PUBLICATIONS

E.E. Nuxoll et al., "BioMEMS Devices for Drug Delivery," IEEE Engineering in Medicine and Biology Magazine, Jan./Feb. 2009, pp. 31-39.

(Continued)

*Primary Examiner* — William R Carpenter
*Assistant Examiner* — William R Frehe
(74) *Attorney, Agent, or Firm* — L. Jeffrey Kelly; Ryan, Mason & Lewis, LLP

(57) ABSTRACT

Electromechanical substance delivery devices are provided which implement low-power electromechanical release mechanisms for controlled delivery of substances such as drugs and medication. For example, an electromechanical device includes a substrate having a cavity formed in a surface of the substrate, a membrane disposed on the surface of the substrate covering an opening of the cavity, and a seal (Continued)

disposed between the membrane and the surface of the substrate. The seal surrounds the opening of the cavity, and the seal and membrane are configured to enclose the cavity and retain a substance within the cavity. An electrode structure is configured to locally heat a portion of the membrane in response to a control voltage applied to the electrode structure, and create a stress that causes a rupture in the locally heated portion of the membrane to release the substance from within the cavity.

14 Claims, 21 Drawing Sheets

(52) U.S. Cl.
CPC .... *A61M 2205/0244* (2013.01); *A61N 1/0428* (2013.01); *A61N 1/0444* (2013.01); *A61N 1/0448* (2013.01)

(58) Field of Classification Search
USPC .................................. 604/502, 890.1, 891.1
See application file for complete search history.

(56) References Cited

U.S. PATENT DOCUMENTS

| | | | |
|---|---|---|---|
| 4,941,205 A | 7/1990 | Horst et al. | |
| 5,366,454 A | 11/1994 | Currie et al. | |
| 5,474,529 A | 12/1995 | Arenberg | |
| 5,606,323 A | 2/1997 | Heinrich et al. | |
| 5,912,632 A | 6/1999 | Dieska et al. | |
| 6,068,853 A | 5/2000 | Giannos et al. | |
| 6,243,013 B1 | 6/2001 | Duan et al. | |
| 6,334,859 B1 | 1/2002 | Richter | |
| 6,436,853 B2* | 8/2002 | Lin ..................... B81C 1/00269 257/682 | |
| 6,551,838 B2 | 4/2003 | Santini, Jr. et al. | |
| 6,593,845 B1 | 7/2003 | Friedman et al. | |
| 6,703,921 B1 | 3/2004 | Wuidart et al. | |
| 6,773,429 B2 | 8/2004 | Sheppard, Jr. et al. | |
| 6,831,548 B1 | 12/2004 | Eber et al. | |
| 6,849,463 B2 | 2/2005 | Santini, Jr. et al. | |
| 6,875,208 B2 | 4/2005 | Santini, Jr. et al. | |
| 6,953,455 B2 | 10/2005 | Cho et al. | |
| 6,969,382 B2 | 11/2005 | Richter | |
| 7,001,372 B2 | 2/2006 | Richter | |
| 7,070,592 B2 | 7/2006 | Santini, Jr. et al. | |
| 7,114,312 B2 | 10/2006 | Coppeta et al. | |
| 7,226,442 B2 | 6/2007 | Sheppard, Jr. et al. | |
| 7,260,371 B1 | 8/2007 | Yones | |
| 7,372,359 B2 | 5/2008 | Wuidart et al. | |
| 7,455,667 B2* | 11/2008 | Uhland ............. A61M 25/0082 604/500 | |
| 7,473,248 B2 | 1/2009 | Santini, Jr. et al. | |
| 7,510,551 B2 | 3/2009 | Uhland et al. | |
| 7,534,241 B2 | 5/2009 | Coppeta et al. | |
| 7,563,255 B2 | 7/2009 | Adamis et al. | |
| 7,587,190 B2 | 9/2009 | Balachandran et al. | |
| 7,598,864 B2 | 10/2009 | Sugimura et al. | |
| 7,642,918 B2 | 1/2010 | Kippelen et al. | |
| 7,652,313 B2 | 1/2010 | Ellis-monaghan et al. | |
| 7,652,557 B2 | 1/2010 | Kantrowitz et al. | |
| 7,791,481 B2 | 9/2010 | Landt et al. | |
| 7,901,397 B2 | 3/2011 | Santini, Jr. et al. | |
| 7,910,151 B2 | 3/2011 | Uhland et al. | |
| 7,983,565 B2 | 7/2011 | Varshneya et al. | |
| 8,083,710 B2 | 12/2011 | Hood et al. | |
| 8,095,197 B2 | 1/2012 | Santini, Jr. et al. | |
| 8,205,800 B2 | 6/2012 | Addy | |
| 8,211,092 B2 | 7/2012 | Uhland et al. | |
| 8,273,610 B2 | 9/2012 | Or-Bach et al. | |
| 8,369,786 B2 | 2/2013 | Witschnig et al. | |
| 8,477,015 B1 | 7/2013 | Pai | |
| 8,924,023 B2 | 12/2014 | Akpan | |
| 9,042,281 B2 | 5/2015 | Miller et al. | |
| 9,108,006 B2 | 8/2015 | Jensen et al. | |
| 9,734,371 B2 | 8/2017 | Friedman et al. | |
| 9,755,701 B2 | 9/2017 | Friedman et al. | |
| 9,937,124 B2 | 4/2018 | Chey et al. | |
| 10,286,198 B2 | 5/2019 | Dang et al. | |
| 2001/0004236 A1 | 6/2001 | Letkomiller et al. | |
| 2001/0051766 A1 | 12/2001 | Gazdzinski | |
| 2003/0175354 A1 | 9/2003 | Drizen et al. | |
| 2003/0198474 A1 | 10/2003 | Mooney et al. | |
| 2004/0020173 A1* | 2/2004 | Cho ..................... A61K 9/0097 53/487 | |
| 2004/0062556 A1 | 4/2004 | Kubo et al. | |
| 2004/0106914 A1 | 6/2004 | Coppeta et al. | |
| 2004/0106953 A1 | 6/2004 | Yomtov et al. | |
| 2004/0166140 A1* | 8/2004 | Santini, Jr. ........... A61K 9/0024 424/424 | |
| 2004/0230182 A1 | 11/2004 | Heruth et al. | |
| 2005/0001724 A1 | 1/2005 | Heinrich et al. | |
| 2005/0050859 A1* | 3/2005 | Coppeta ............... A61K 9/0097 53/471 | |
| 2005/0055014 A1 | 3/2005 | Coppeta et al. | |
| 2005/0061870 A1 | 3/2005 | Stockton | |
| 2005/0096587 A1 | 5/2005 | Santini, Jr. et al. | |
| 2005/0143715 A1 | 6/2005 | Cima et al. | |
| 2005/0152261 A1 | 7/2005 | Kahlman | |
| 2005/0206504 A1 | 9/2005 | Sugimura et al. | |
| 2005/0240370 A1 | 10/2005 | Diorio et al. | |
| 2006/0024358 A1* | 2/2006 | Santini, Jr. ............. A61K 9/703 424/448 | |
| 2006/0057737 A1* | 3/2006 | Santini, Jr. ........... A61K 9/0097 436/174 | |
| 2006/0105275 A1* | 5/2006 | Maloney ............. A61K 9/0024 430/320 | |
| 2006/0115323 A1* | 6/2006 | Coppeta ............... A61K 9/0097 403/270 | |
| 2006/0127097 A1 | 6/2006 | Obrea et al. | |
| 2006/0222134 A1 | 10/2006 | Eldredge et al. | |
| 2006/0248576 A1 | 11/2006 | Levinson | |
| 2006/0284770 A1 | 12/2006 | Jo et al. | |
| 2007/0015549 A1 | 1/2007 | Hernandez et al. | |
| 2007/0050683 A1 | 3/2007 | Attinella et al. | |
| 2007/0096880 A1 | 5/2007 | Nagai | |
| 2007/0103311 A1 | 5/2007 | Kippelen et al. | |
| 2007/0230322 A1 | 10/2007 | Morita | |
| 2007/0253137 A1 | 11/2007 | Maloney | |
| 2007/0273485 A1 | 11/2007 | Balachandran et al. | |
| 2008/0042043 A1 | 2/2008 | Reime et al. | |
| 2008/0088417 A1 | 4/2008 | Smith et al. | |
| 2008/0094245 A1 | 4/2008 | Hardacker et al. | |
| 2008/0154230 A1 | 6/2008 | Subramony et al. | |
| 2008/0231458 A1 | 9/2008 | Fein | |
| 2008/0244273 A1 | 10/2008 | Chen et al. | |
| 2009/0099553 A1* | 4/2009 | Langereis ............. A61K 9/0097 604/891.1 | |
| 2009/0202254 A1 | 8/2009 | Majumdar et al. | |
| 2009/0275925 A1* | 11/2009 | Langereis ............. A61K 9/0019 604/891.1 | |
| 2009/0294535 A1 | 12/2009 | Paeschke et al. | |
| 2009/0306633 A1 | 12/2009 | Trovato et al. | |
| 2010/0061734 A1 | 3/2010 | Knapp | |
| 2010/0128749 A1 | 5/2010 | Amann et al. | |
| 2010/0182160 A1 | 7/2010 | Lu | |
| 2010/0328043 A1 | 12/2010 | Jantunen et al. | |
| 2011/0053503 A1 | 3/2011 | Witschnig et al. | |
| 2011/0108616 A1 | 5/2011 | Wang | |
| 2011/0163852 A1 | 7/2011 | Kanda et al. | |
| 2011/0188800 A1 | 8/2011 | Futami | |
| 2011/0205134 A1 | 8/2011 | Blumberg, Jr. | |
| 2011/0215156 A1 | 9/2011 | Johnson, II et al. | |
| 2011/0318013 A1 | 12/2011 | Primm | |
| 2012/0013446 A1 | 1/2012 | Ino | |
| 2012/0032785 A1 | 2/2012 | Kamata | |
| 2012/0153910 A1 | 6/2012 | Bulzacchelli et al. | |
| 2012/0161338 A1 | 6/2012 | Lowenthal et al. | |
| 2012/0234922 A1 | 9/2012 | Sample et al. | |
| 2012/0245565 A1 | 9/2012 | Shachar et al. | |
| 2012/0294625 A1 | 11/2012 | Dynes et al. | |

(56) References Cited

U.S. PATENT DOCUMENTS

| | | |
|---|---|---|
| 2013/0030763 A1 | 1/2013 | Mazzillo |
| 2013/0106607 A1 | 5/2013 | Clement et al. |
| 2013/0150689 A1* | 6/2013 | Shaw-Klein ......... A61B 5/6821 600/345 |
| 2013/0206837 A1 | 8/2013 | Szu |
| 2013/0216219 A1 | 8/2013 | Honda et al. |
| 2013/0285795 A1 | 10/2013 | Virtanen et al. |
| 2014/0015642 A1 | 1/2014 | White |
| 2014/0016945 A1 | 1/2014 | Pan |
| 2014/0022057 A1 | 1/2014 | Trosper |
| 2014/0296773 A1 | 10/2014 | Bulent et al. |
| 2014/0332663 A1 | 11/2014 | Zecri |
| 2015/0102908 A1 | 4/2015 | Griesmann et al. |
| 2015/0162984 A1 | 6/2015 | Liu et al. |
| 2015/0227766 A1 | 8/2015 | Koezuka et al. |
| 2015/0272830 A1 | 10/2015 | Iordanov et al. |
| 2015/0310715 A1 | 10/2015 | Nekoogar et al. |
| 2015/0382425 A1 | 12/2015 | Lewis et al. |
| 2016/0074323 A1 | 3/2016 | Chey et al. |
| 2016/0117583 A1 | 4/2016 | Butler et al. |
| 2016/0119059 A1 | 4/2016 | Chandra et al. |
| 2016/0242124 A1 | 8/2016 | Zhou et al. |
| 2016/0292470 A1 | 10/2016 | Friedman et al. |
| 2016/0294481 A1 | 10/2016 | Friedman et al. |
| 2017/0105260 A1 | 4/2017 | Ho et al. |
| 2017/0119960 A1 | 5/2017 | Dang et al. |
| 2017/0140182 A1 | 5/2017 | Mizuno |
| 2017/0147915 A1 | 5/2017 | Butler et al. |
| 2017/0228568 A1 | 8/2017 | Friedman et al. |
| 2017/0272125 A1 | 9/2017 | Friedman et al. |
| 2017/0325746 A1 | 11/2017 | Niichel et al. |

FOREIGN PATENT DOCUMENTS

| | | |
|---|---|---|
| CN | 202711296 U | 1/2013 |
| CN | 203562013 U | 4/2014 |
| CN | 103955736 A | 7/2014 |
| JP | 2013061888 A | 4/2013 |
| KR | 20090098472 A | 9/2009 |
| WO | 2008091826 A1 | 7/2008 |
| WO | 2009064402 A1 | 5/2009 |
| WO | 2009107136 A2 | 9/2009 |

OTHER PUBLICATIONS

Knowles, "New Product: Ultrasonic MEMS Microphone," http://www.knowles.com/eng/Newsroom/New-product-Ultrasonic-MEMS-Microphone, Feb. 1, 2016, 2 pages.

R. Colin Johnson, "MEMS Mics Taking Over, Tasks Once Performed by Specialized Chips," EETimes, http://www.eetimes.com/document.asp?doc_id=1324827, Dec. 2, 2014, 3 pages.

Focused Ultrasound Foundation, "Overview," http://www.fusfoundation.org/the-technology/overview, Feb. 1, 2016, 2 pages.

S. Roy et al., "RFID: From Supply Chains to Sensor Nets," Proceedings of the IEEE, Jul. 2010, pp. 1583-1592, vol. 98, No. 9.

M. Buckner et al., "GPS and Sensor-Enabled RFID Tags," Unclassified Document, Oak Ridge National Laboratory, http://www.oml.gov/webworks/cppr/y2001/pres/118169.pdf, 2001, 5 pages.

A.P. Sample et al., "Design of a Passively-Powered, Programmable Sensing Platform for UHF RFID Systems," IEEE International Conference on RFID, Mar. 2007, pp. 149-156.

J. M. Maloney et al., "Electrothermally Activated Microchips for Implantable Drug Delivery and Biosensing," Science Direct, Journal of Controlled Release vol. 109, Issues 1-3, Dec. 2005, pp. 244-255.

L. Hu et al., "A Composite Thermo-Responsive Membrane System for Improved Controlled-Release," Chemical Engineering & Technology, vol. 30, No. 4, 2007, pp. 523-529.

Fritz et al., "Thresholds for Igniting Exothermic Reactions in Al/Ni Multilayers Using Pulses of Electrical, Mechanical, and Thermal Energy," Jorunal of Applied Physics, vol. 113, No. 1, 2013, 12 pages.

* cited by examiner

100

200

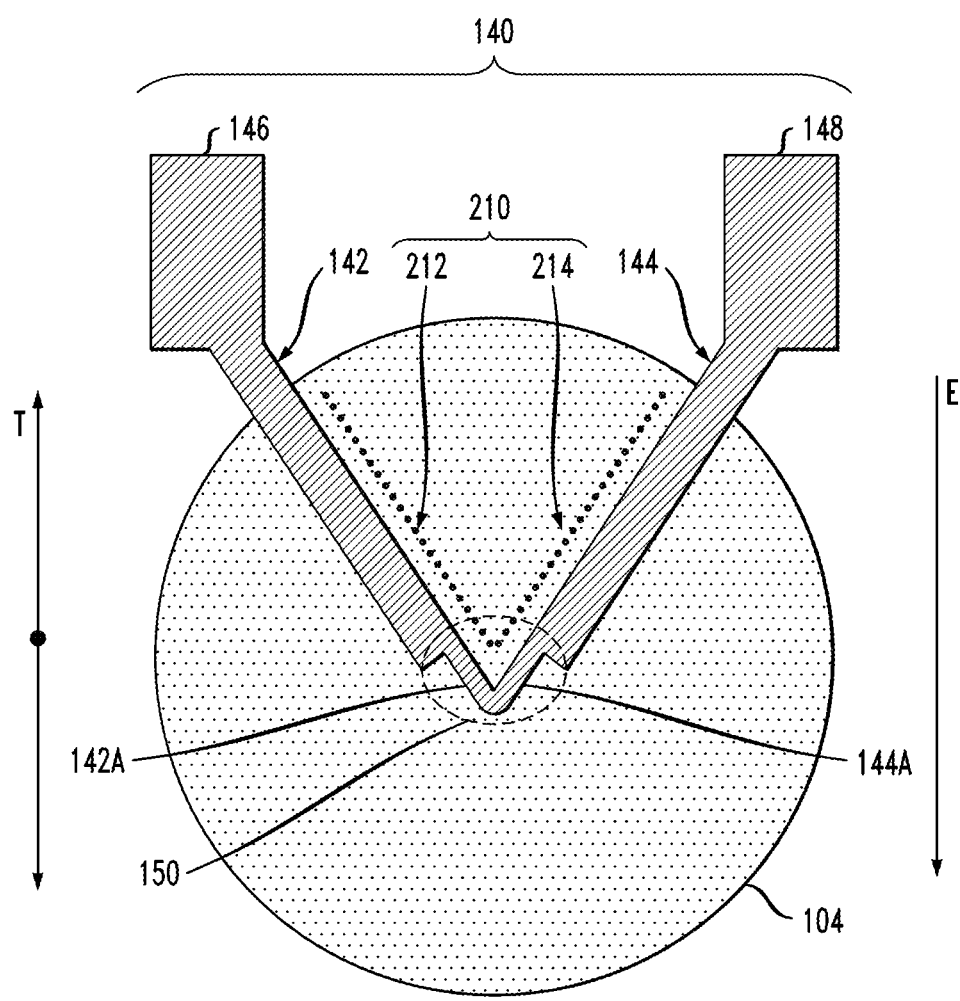

400

500

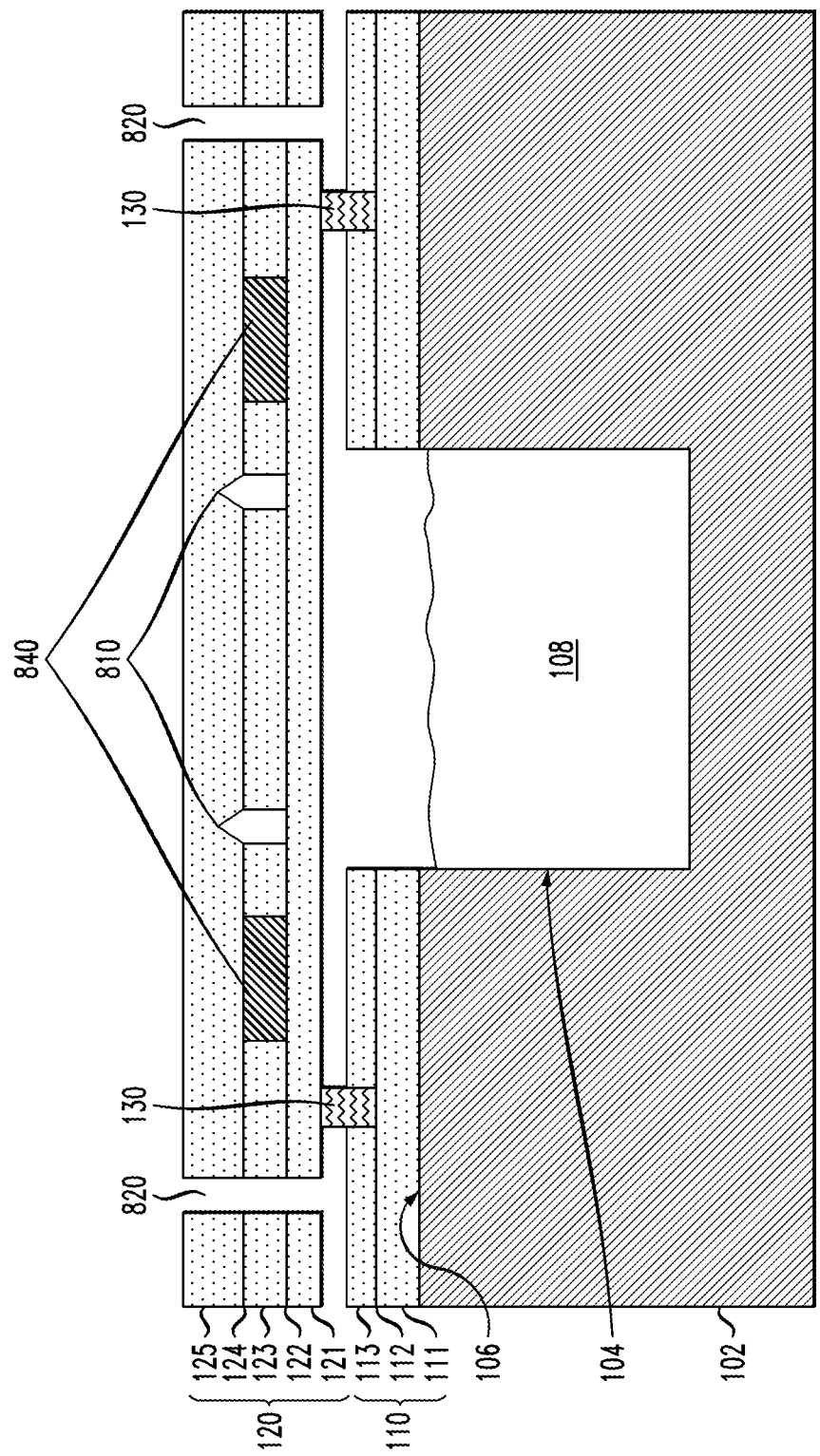

1200

1300

1300

1400

MICROCHIP SUBSTANCE DELIVERY DEVICES

TECHNICAL FIELD

This application generally relates to micro-electromechanical devices and, in particular, to micro-electromechanical substance delivery devices and methods for controlled delivery of substances such as drugs and medication.

BACKGROUND

In recent years, there has been significant research and development in the biomedical field with regard to drug delivery devices and, in particular, implantable bio-compatible microchip drug delivery devices. In general, an implantable microchip drug delivery device includes an array of micro-scale reservoirs that are formed in a substrate. The reservoirs are filled with certain medications/drugs that are contained within the reservoirs using releasable membrane structures. The microchip drug delivery devices are designed with various types of actuation mechanisms that allow the contents of the reservoirs to be automatically released (via the releasable membrane structures) either continuously, periodically or "on demand" by an individual (e.g., doctor or patient). These actuation mechanisms generally include passive and active release mechanisms.

By way of example, with passive release mechanisms, porous releasable membrane structures can be utilized which allow the contents of the reservoirs to slowly diffuse out from the reservoirs. Alternatively, a passive release mechanism can be configured to deteriorate over time to release the reservoir contents. Furthermore, an example of an active release mechanism includes releasable membranes that are configured to rupture using electrical actuation mechanisms. In general, these active release mechanisms utilize a power source, such as a thin-film battery, to provide an electrical current and/or voltage that is sufficient to rupture or otherwise melt or vaporize a membrane structure to thereby provide controlled release of reservoir contents. When drug delivery over a long period of time is required, it is necessary to minimize the energy requirements for active release mechanisms to ensure proper device operation, as well as minimize any adverse impact of the power dissipation on the reservoir contents to be released as well as organism cell function. Although a variety of active reservoir release methods have been proposed, none of the proposed methods implement low-power release mechanisms for rupturing releasable structures.

SUMMARY

In general, embodiments of the invention include electromechanical substance delivery devices and methods implementing low-power electromechanical release mechanisms for controlled delivery of substances such as drugs and medication. In one embodiment of the invention, an electromechanical device includes a substrate having a cavity formed in a surface of the substrate, a membrane disposed on the surface of the substrate covering an opening of the cavity, and a seal disposed between the membrane and the surface of the substrate. The seal surrounds the opening of the cavity, and the seal and membrane are configured to enclose the cavity and retain a substance within the cavity. The device further includes an electrode structure that is configured to locally heat a portion of the membrane in response to a control voltage applied to the electrode structure, and create a stress that causes a rupture in the locally heated portion of the membrane to release the substance from within the cavity.

In another embodiment of the invention, an electromechanical device includes a substrate having a cavity formed in a surface of the substrate, a membrane disposed on the surface of the substrate covering an opening of the cavity, and a seal disposed between the membrane and the surface of the substrate. The seal surrounds the opening of the cavity, and the seal and membrane are configured to enclose the cavity and retain a substance within the cavity. The device further includes an electrode structure having a first contact, a second contact, and a plurality of filaments arranged adjacent to each other. The plurality of filaments are electrically connected in parallel to the first and second contacts of the electrode structure, and the filaments are configured to melt in succession in response to a control voltage applied to the first and second contacts, and cause a rupture in a portion of the membrane adjacent to the plurality of filaments to release the substance from within the cavity.

In yet another embodiment of the invention, an electromechanical device includes a substrate comprising a cavity formed in a surface of the substrate, and a membrane disposed on the surface of the substrate covering an opening of the cavity. The membrane includes a plurality of voids formed within the membrane, wherein the plurality of voids are configured to reduce a strength of the portion of the membrane within which the voids are formed. A seal is disposed between the membrane and the surface of the substrate, wherein the seal surrounds the opening of the cavity, wherein the seal and membrane are configured to enclose the cavity and retain a substance within the cavity. The device further includes an electrode structure configured to thermally expand in response to a control voltage applied to the electrode structure and apply a tensile stress to the portion of the membrane within which the voids are formed and cause a rupture in said portion of the membrane to release the substance from within the cavity.

In another embodiment of the invention, an electromechanical device includes a substrate comprising a cavity formed in a surface of the substrate, a metallic membrane disposed on the surface of the substrate covering an opening of the cavity, and a seal disposed between the metallic membrane and the surface of the substrate, wherein the seal surrounds the opening of the cavity, and wherein the seal and metallic membrane are configured to enclose the cavity and retain a substance within the cavity. The device further includes an electrode structure configured to locally heat a portion of the metallic membrane in response to a control voltage applied to the electrode structure, and cause melting of the locally heated portion of the metallic membrane to release the substance from within the cavity.

In yet another embodiment of the invention, an electromechanical device includes a substrate comprising a cavity formed in a surface of the substrate, a membrane disposed on the surface of the substrate covering an opening of the cavity, and a seal disposed between the membrane and the surface of the substrate, wherein the seal surrounds the opening of the cavity, wherein the seal and membrane are configured to enclose the cavity and retain a substance within the cavity. The device further includes an electrode structure formed on the membrane, wherein the electrode structure is formed in a tensile-stressed state, and comprises a fuse portion. The membrane includes a plurality of voids formed within the membrane along one or more edges of the electrode structure, wherein the plurality of voids are configured to reduce a strength of a portion of the membrane along the one or more edges of the electrode structure. The fuse portion of the electrode structure is configured to melt in response to a control voltage applied to the electrode structure and cause the electrode structure to peel back and rupture the portion of the membrane in which the plurality of voids are formed along the one or more edges of the electrode structure.

In yet another embodiment of the invention, an electromechanical device includes a substrate comprising a cavity formed in a surface of the substrate, a membrane disposed on the surface of the substrate covering an opening of the cavity, and a seal disposed between the membrane and the surface of the substrate, wherein the seal surrounds the opening of the cavity, and wherein the seal and membrane are configured to enclose the cavity and retain a substance within the cavity. The device further includes an electrode structure configured to locally heat a least a portion of the seal in response to a control voltage applied to the electrode structure, and melt the locally heated portion of the seal to release the substance from within the cavity.

In another embodiment of the invention, an electromechanical device includes a substrate comprising a cavity formed in a surface of the substrate, a membrane disposed on the surface of the substrate covering an opening of the cavity, and a seal disposed between the membrane and the surface of the substrate, wherein the seal surrounds the opening of the cavity, and wherein the seal and membrane are configured to enclose the cavity and retain a substance within the cavity. The device further includes an electrode structure configured to locally heat a region in proximity to the seal in response to a control voltage applied to the electrode structure, and cause a mechanical stress that is effective to break at least a portion of the seal to release the substance from within the cavity.

These and other embodiments of the invention will be described or become apparent from the following detailed description of embodiments, which is to be read in conjunction with the accompanying drawings.

BRIEF DESCRIPTION OF THE DRAWINGS

FIGS. 2A and 2B schematically illustrate a microchip substance delivery device having a low-power electromechanical release mechanism, according to another embodiment of the invention.

FIGS. 8A and 8B schematically illustrate a microchip substance delivery device having a low-power electromechanical release mechanism, according to another embodiment of the invention.

DETAILED DESCRIPTION

Embodiments of the invention will now be discussed in further detail with regard to microchip substance delivery devices having low-power electromechanical release mechanisms to provide controlled delivery of substances such as drugs and medication. In general, embodiments of the invention include electromechanical releasable membrane structures that incorporate microelectronic structures within a releasable membrane to effectively provide low-energy actuation mechanisms that allow precise control of the release location within the membrane. For example, embodiments of the invention include electrode structures that confine electrical current to small regions of a releasable membrane structure to cause localized heating within the small regions of releasable membrane structure. This localized heating introduces mechanical stress in the locally heated regions of the membrane to initiate membrane rupturing due to a highly localized thermal energy density, thereby providing a low-power actuation mechanism with precise control of the rupture location of the membrane.

As discussed in further detail below, the exemplary microchip substance delivery devices described herein can be constructed using standard MEMS (Micro-Electro-Mechanical-Systems) fabrication techniques, as well as wafer-level 3D fabrication and integration techniques, to construct a device substrate having array of micro reservoirs to store deliverable substances (such as drugs or medications), as well as to construct layered releasable membranes with integrated electrode structures to seal the deliverable substances within the cavities of the device substrate. Indeed, various components and structures of microchip substance delivery devices according to embodiments of the invention can be fabricated using a combination of standard processes, namely semiconductor lithography, MEMs processes, and low-temperature wafer-to-wafer three-dimensional silicon processes, and using standard materials and structures that are compatible with back-end-of-the-line (BEOL) processing, wafer bonding, wafer thinning, and wafer transfer processes.

It is to be understood that the various layers, structures, and regions shown in the accompanying drawings are not drawn to scale, and that one or more layers, structures, and regions of a type commonly used in microchip substance delivery devices may not be explicitly shown in a given drawing. This does not imply that the layers, structures, and regions not explicitly shown are omitted from the actual microchip substance delivery devices. Moreover, the same or similar reference numbers used throughout the drawings are used to denote the same or similar features, elements, or structures, and thus, a detailed explanation of the same or similar features, elements, or structures will not be repeated for each of the drawings.

Figure 1A:
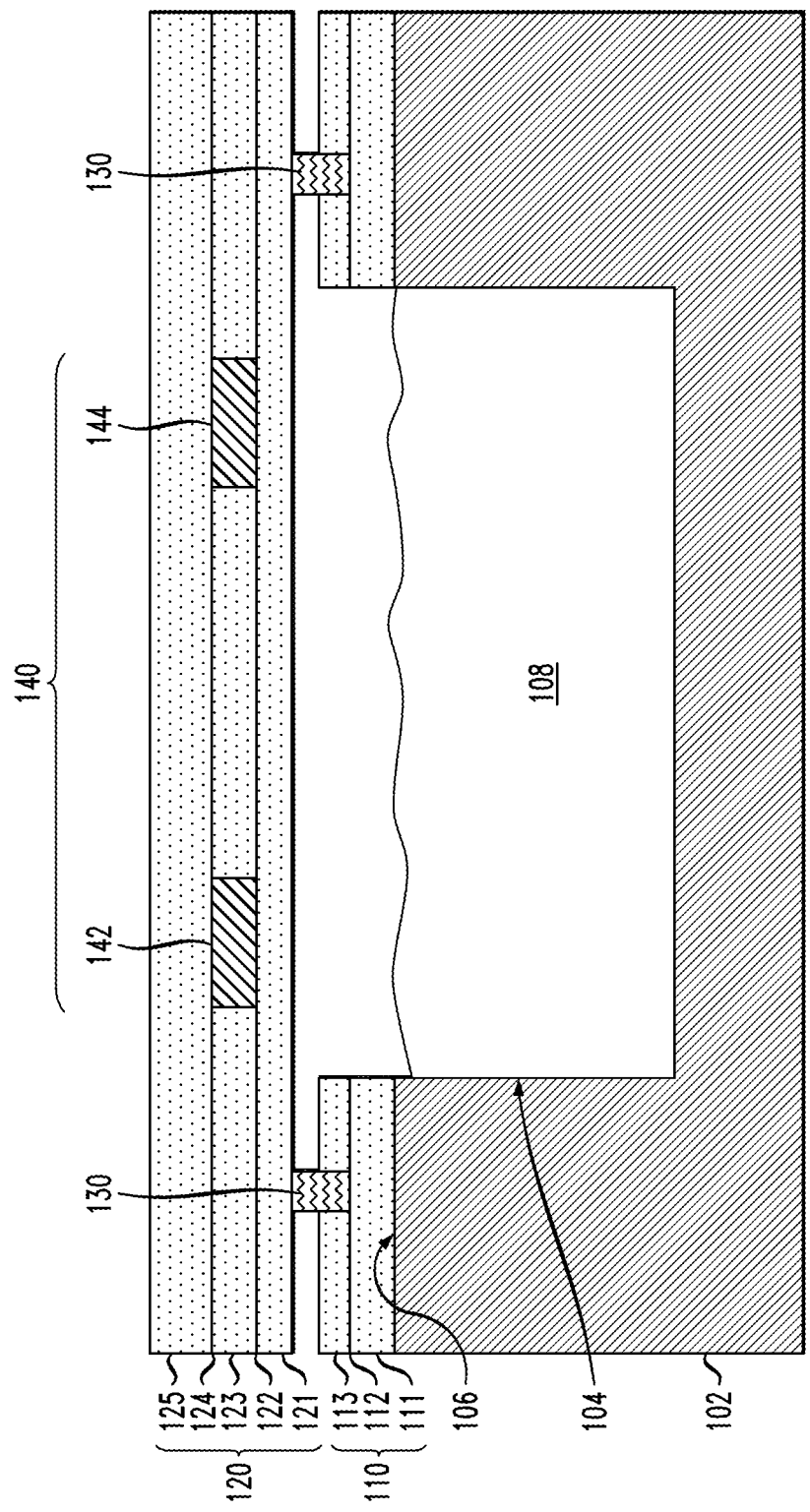
FIGS. 1A and 1B schematically illustrate a microchip substance delivery device having a low-power electromechanical release mechanism, according to an embodiment of the invention.
Figure 1B:
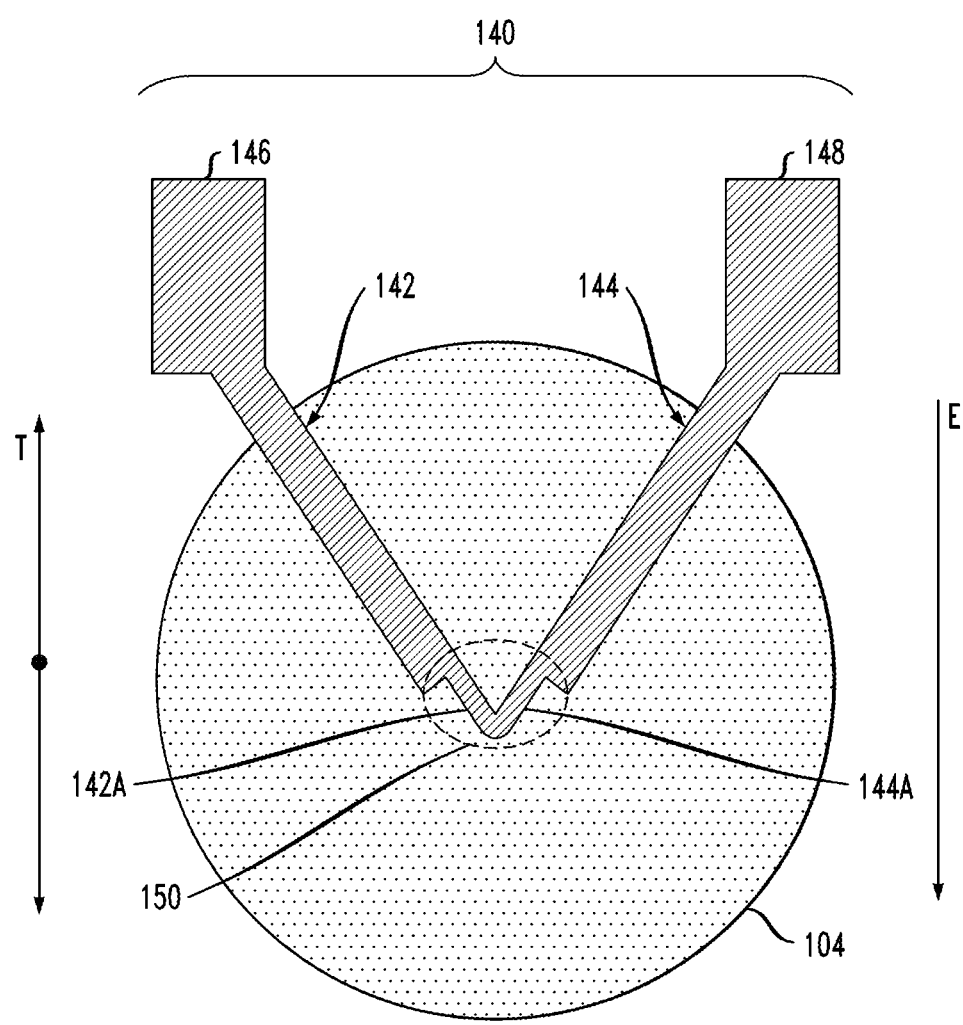

FIGS. 1A and 1B schematically illustrate a microchip substance delivery device having a low-power electromechanical release mechanism, according to an embodiment of the invention. In particular, FIG. 1A is a schematic side view of a microchip substance delivery device 100, and FIG. 1B is a schematic top plan view of a portion of the microchip substance delivery device 100 of FIG. 1A. As shown in FIG. 1A, the microchip substance delivery device 100 comprises a substrate 102 and a cavity 104 formed in a surface 106 of the substrate 102. The cavity 104 is filled with a deliverable substance 108 such as a medication or drug in liquid or solid form, for example. The substrate 102 further comprises a plurality of insulating layers 110 (which are part of a BEOL structure) formed on the surface 106 of the substrate 102. In the example embodiment of FIG. 1A, the insulating layers 110 include, for example, a stack of layers including a silicon dioxide layer 111, a silicon nitride layer 112, and a silicon dioxide layer.

The microchip substance delivery device 100 further comprises a membrane 120 disposed on the substrate 102 covering an opening of the cavity 104, and a seal 130 disposed between the membrane 120 and the surface 106 of the substrate 102. The seal 130 surrounds the opening of the cavity 104. The seal 130 and the membrane 120 are configured to enclose the cavity 104 and retain the substance 108 within the cavity 104. While only one cavity 104 is shown for illustrative purposes, it is to be understood that the substrate 102 may be formed with an array of cavities comprising hundreds of cavities that serve as reservoirs for holding the same type or a combination of different types of deliverable substances.

In addition, as collectively shown in FIGS. 1A and 1B, the microchip substance delivery device 100 further comprises an electrode structure 140 that is integrally formed as part of the membrane 120. As specifically shown in FIG. 1A, in one embodiment of the invention, membrane 120 is formed of multiple layers of insulating material including, for example, thin silicon dioxide layers 121, 123, 125, and thin silicon nitride layers 122 and 124 disposed between the silicon dioxide layers 121, 123, 125. The electrode structure 140 comprises a patterned layer of a metallic material such as copper, having electrode elements formed in one or more of the silicon dioxide layers 121, 123 and 125. As explained in further detail below, in one embodiment of the invention, the electrode structure 140 is configured to locally heat a portion 150 of the membrane 120 in response to a control voltage applied to the electrode structure 140 (via control circuitry discussed below with reference to FIG. 15). This localized heating of the membrane 120 creates a mechanical stress in the locally heated portion 150 of the membrane 120 which is sufficient to cause a rupture in the locally heated portion 150 of the membrane 120 and release the substance 108 from within the cavity 104.

More specifically, FIG. 1B is a partial top plan view that illustrates an exemplary pattern of the electrode structure 140 as formed within the silicon dioxide layer 123 of the membrane 120, as well as position of the electrode structure 140 with regard to a perimeter of the opening of the cavity 104. In the embodiment shown in FIG. 1B, the electrode structure 140 comprises a V-shaped electrode 142/144, a first contact 146 and a second contact 148. The V-shaped electrode 142/144 comprises a first leg 142 and a second leg 144. The first and second contacts 146 and 148 serve as anode/cathode contacts that receive a control voltage from control circuitry which is connected to the first and second contacts 146 and 148 using wiring structures such as metallic vias and traces that are formed through and within other layers of the membrane 120 and/or other metallization that is formed as part of the BEOL 110 of the microchip substance delivery device 100.

The first leg 142 extends from the first contact 146 and includes an end portion 142A that is thinner in width than the width of the first leg 142. Similarly, the second leg 144 extends from the second contact 148 and includes an end portion 144A that is thinner in width than the width of the second leg 142. The end portions 142A and 144A of the first and second legs 142 and 144 form an "apex" portion of the V-shaped electrode 142/144 which is configured to provide localized heating of the portion 150 of the membrane 120. More specifically, when a control voltage is applied to the first and second contacts 146 and 148, the current flow through the V-shaped electrode 142/144 will have a higher current density in the apex region 142A/144A because of the thinner width metallization pattern and the angled shape of the apex region 142A/144A. This higher current density in the apex region 142A/144A results in a high thermal density in the locally heated portion 150 of the membrane 120 surrounding the apex region 142A/144A. This localized high thermal density causes a mechanical stress in the locally heated portion 150 of the membrane 120 which is sufficient to rupture the membrane 120.

More specifically, the electrode structure 140 shown in FIG. 1B provides a low-energy release mechanism with precise control of the release location on the membrane 120. When properly designed, sufficient heat can be generated in the locally heated region 150 of the membrane 120 by the application of a pulsed control voltage (as compared to a continuous DC voltage). Indeed, since the thinner profile apex region 142A/144A focusses current density in the locally heated region 150, the application of a pulsed voltage is sufficient to cause significant heating and expansion of the insulating material in the locally heated region 150 of the membrane 120 and induce membrane rupture in the locally heated region 150. The high current density flowing through the apex region 142A/144A of the electrode 140 confines the high thermal density to the small local region 150 of the membrane 120 to provide a more precise control of the rupturing location of the membrane 120 due to the increased localized energy density in the locally heated portion 150.

In one embodiment of the invention, the electrode structure 140 is designed so that the locally heated portion 150 of the membrane 120 has a lateral dimension that is less than about two times a thickness of the membrane 120. In other words, to achieve low-power release, the region of membrane 120 which is locally heated is restricted in size to an area much smaller than the size of the cavity 104 (which is in contrast to other release schemes that are designed to heat an area of the membrane which is the same as the area of the cavity opening). The size of the locally heated portion 150 of the membrane 120 (in relation to the thickness of the membrane 120) will vary depending on the material(s) used to form the membrane 120 and whether the membrane 120 is formed in a non-stressed state or a stressed state.

More specifically, in one embodiment of the invention, the membrane 120 can be formed in a non-stressed state (e.g., no tensile stress), such that rupture of the membrane 120 is caused by the mechanical stress that is induced in the membrane 120 by virtue of the localized heating of a small portion of the membrane, as discussed above. In addition, in the embodiment of FIG. 1B, depending on the CTE (coefficient of thermal expansion) of the material used to form the electrode structure 140, when current flows through the electrode structure 140, an expansion force (denoted by arrow E in FIG. 1B) can also be imparted to the membrane 120 by virtue of heating and thermal expansion of the electrode structure 140. The expansion force E exerted by the electrode structure 140 on the membrane 120, coupled with the mechanical stress caused by the localized heating of the membrane 120, can assist in causing a rupture in the locally heated portion 150 of the membrane 120.

In another embodiment of the invention, low-power release is further achieved by forming one or more thin film layers (e.g., the silicon nitride layers 122, 124) of the membrane 120 in a state of internal tensile stress, which stresses the membrane 120 close to the elastic limit. In other words, the internal stress can be formed to a level that is close to, but does not exceed, a stress level which would cause spontaneous cracking and rupture of the membrane 120. By way of specific example, as shown in FIG. 1B, the membrane 120 can be formed with a tensile stress emanating from a central region of the membrane 120 (as indicated by the arrow T). In this embodiment, the tensile stress T of the membrane 120, the thermal expansion force E of the electrode structure 140, and the mechanical stress in the locally heated region 150 of the membrane, collectively provide a force that is sufficient to cause a rupture in at least the locally heated region 150 of the membrane 120. The apex 142A/144A of the V-shaped electrode 142/144 can be located near the center of the membrane 120, where maximum tensile pre-stress is present. Alternatively, the apex 142A/144A of the V-shaped electrode 142/144 can be located closer to the edge of the cavity 140 to increase the size of the opening. Indeed, when the membrane 120 is formed in a pre-stressed tensile state, once rupture occurs in the locally heated region 150, the tensile stress of the membrane 120 can cause portions of the membrane 120 to peel back away from the ruptured region of the membrane 120.

As noted above, microchip substance delivery devices according to embodiments of the invention can be fabricated using standard materials and semiconductor fabrication processes, including MEMS technology, and BEOL, photolithography, wafer bonding, wafer thinning, and wafer transfer processes, for example. Moreover, the materials used for constructing microchip substance delivery devices are preferably materials that are biocompatible or which can otherwise be made biocompatible by coating the materials with suitable biocompatible materials.

For example, the substrate 102 can be formed using any standard semiconductor material such as silicon, glass, ceramic, etc., which can be machined and etched using standard etching processes (e.g., deep reactive ion etching) and wafer thinning processes, for example. The substrate 102 is formed using a biocompatible material, such as silicon, which is not permeable to the liquid contents contained in the etched cavities and bodily fluids of an individual. The dimensions of the cavity 104 and the number of cavities formed in the substrate 102 will vary depending on the application. In one embodiment of the invention, the cavities are circular-shaped cavities that are formed in a silicon substrate using a deep RIE process. In other embodiments, the cavities can be rectangular-shaped. However, with rectangular-shaped cavities, there can be significant surface tension in the corner wall regions of the cavities, whereby the surface area of such corner wall regions may not "wet" well when filling the cavities with liquid content, thereby resulting in the formation of air bubbles along the corner wall regions of the cavities. On the other hand, a circular-shaped cavity eliminates such corner regions and facilities the cavity filling process.

The stack of insulating layers 110 (or BEOL structure) can be formed on the surface 106 of the substrate 102 using standard semiconductor BEOL fabrication processes. The BEOL 110 can be formed to include metal traces that connect the electrode structure 140 with control circuitry that is integrally formed on the microchip substance delivery device 100. The seal 130 can be fabricated using different types of suitable materials and structures. For example, in one embodiment of the invention, referring to FIG. 1A, a portion of the seal 130 is embedded within the silicon dioxide layer 113 of the BEOL 110. This embedded portion of the seal 130 may be a ring of copper material that is formed within an etched trench in the silicon dioxide layer 113 using a standard copper damascene process. An upper portion of the seal 130 can be ring of solder material (e.g., a low melting point solder such as tin, indium, or an tin/indium alloy, for example) which is formed on the membrane 120 in alignment to the copper ring portion of the seal 130 formed in the silicon dioxide layer 113. The seal 130 can be formed by bonding the solder ring on the bottom surface of the membrane 120 to the copper ring formed in the BEOL 110. In other embodiments of the invention, the seal 130 can be formed of a polymer material or other suitable adhesive material. In another embodiment of the invention, the seal 130 can be formed with separate "tongue and groove" components formed on the substrate 102 and membrane 120, respectively.

In one embodiment of the invention, the cavities in the substrate 102 are filled with a deliverable substance prior to the sealing process wherein the membrane 120 is bonded to the substrate 102 via the seal 130. In such instances, the sealing process implemented is one that does not adversely affect or otherwise disturb or degrade the deliverable substance which is filled within the cavities.

In one embodiment of the invention, as noted above, the membrane 120 comprises alternating layers of insulating materials, e.g., silicon dioxide and silicon nitride, which can be fabricated using a standard BEOL process. For example, the membrane 120 is formed on a handler substrate using standard BEOL and copper damascene processes to deposit the insulating layers and form the electrode elements that are embedded within the membrane 120. The membrane 120 can then be transferred to the substrate 102 using a standard wafer transfer/debonding process, and sealed to the substrate 102 using a suitable sealing process to form the seal 130, as discussed above. The silicon nitride films 122 and 124 can be formed in a pre-stressed state, e.g., tensile stress or other suitable stress pattern, to provide the desired stresses that facilitate rupturing of the membrane using actuation mechanisms as described herein.

In other embodiments of the invention, depending on the application, the membrane can be formed with other low thermal conductive, and flexible materials such as polymer materials, which can rupture at specific points that are subjected to highly localized heating, using techniques as described herein. In such embodiments, one or more thin, stressed layers of metallic material can be formed as part of the membrane structure to impart a desired tensile stress (or other stress patterns) to facilitate rupturing of the membrane via a "peel back" force imparted on the membrane due to the stressed metallic layers. In such embodiments, insulating layers would be formed as part of the membrane, as necessary, to electrically isolate the stressed metallic layers from the electrode elements.

Figure 2A:
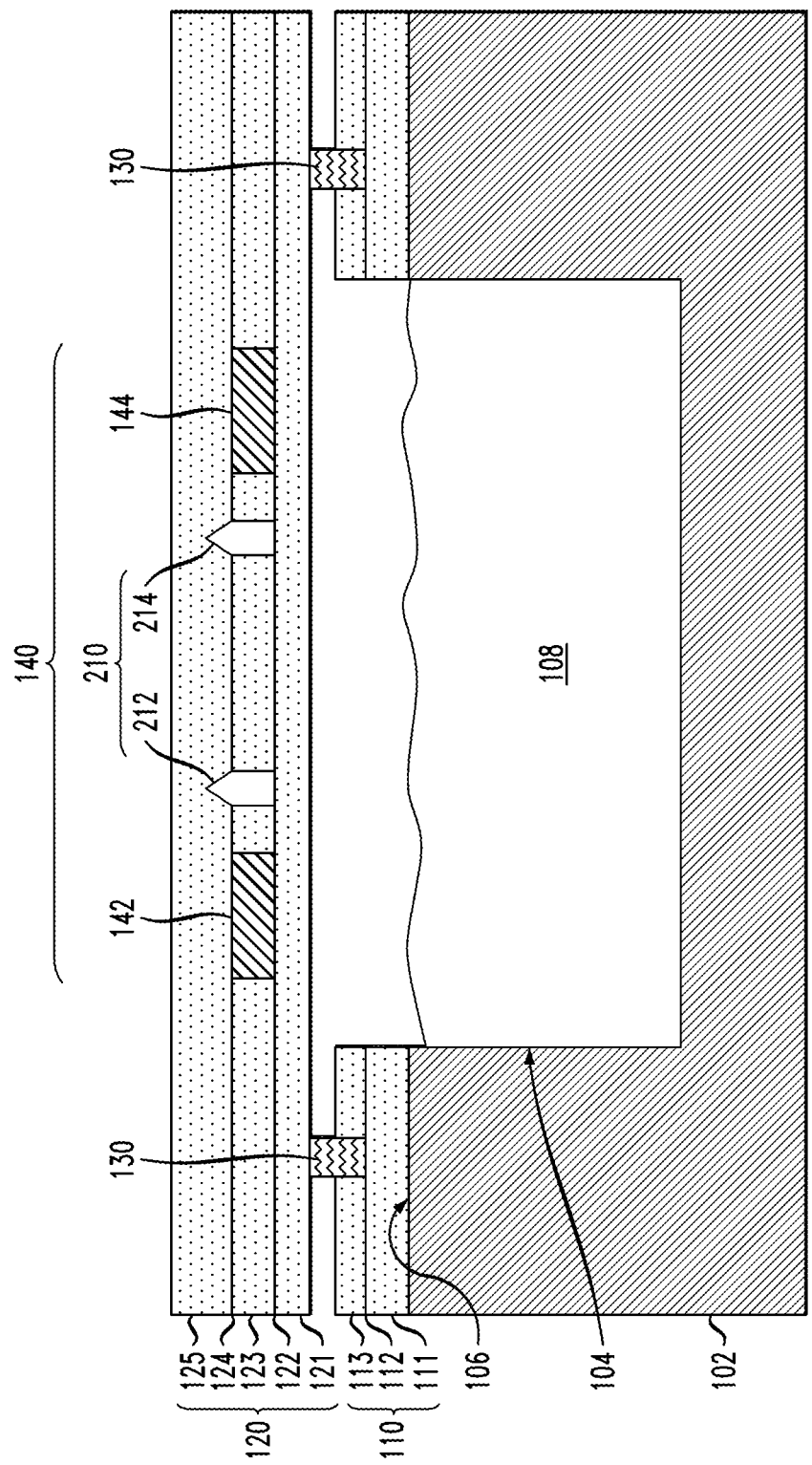

FIGS. 2A and 2B schematically illustrate a microchip substance delivery device having a low-power electromechanical release mechanism, according to another embodiment of the invention. In particular, FIGS. 2A and 2B illustrate a microchip substance delivery device 200 which is similar to the device 100 of FIGS. 1A and 1B, except that the device 200 comprises a plurality of voids (or perforations) 210 formed in the membrane 120 to facilitate rupturing of the membrane 120 in addition to the mechanisms discussed above with reference to FIGS. 1A and 1B.

As specifically shown in FIG. 2A, in an embodiment where the membrane 120 is formed of multiple thin film layers of insulating material, a plurality of voids 210 (or perforations) can be formed within the inner layers of the membrane 120 to provide localized regions of mechanical weakness in the membrane 120 to facilitate rupturing. The voids 210 comprise a series of pinched-off perforations formed within the membrane 120. The voids 210 can be formed by standard lithographic processes using reactive ion etching to etch via cavities in one or more inner insulating layers of the membrane 120, wherein the via cavities are then "pinched-off" by depositing a thin film of insulating material using a plasma-enhanced vapor deposition process, which does not fill the via cavities.

For example, as shown in FIG. 2A, the voids 210 are formed by etching via cavities through the silicon dioxide 123 and silicon nitride 124 layer, and then closing off the top of the via cavities by deposition of the silicon dioxide layer 125. In one embodiment of the invention, a lateral dimension of the voids 210 should be about the same as the thickness of the membrane 120, and the vertical dimension of the voids 210 should be as close to the thickness of the membrane 120 as possible, which can be robustly pinched-off and sealed.

As shown in FIGS. 2A and 2B, a plurality of voids 212 are formed near the first leg 142 of the V-shaped electrode 142/144 and a plurality of voids 214 are formed near the second leg 144 of the V-shaped electrode 142/144. As specifically shown in FIG. 2B, the plurality of voids 212 and 214 each comprises a linear array of perforations that extend along inner edges of the V-shaped electrode 142/144 into the locally heated region 150 of the membrane 120, forming a void "apex". In the embodiment of FIG. 2B, the voids 212 and 214 form a V-shaped line of weakness which facilitate the rupturing of the membrane 120. In particular, since the voids are located along the inner edges of the first and second legs 142 and 144 of the V-shaped electrode, the voids 212 and 214 undergo additional tensile stress upon heating, and cracks are first initiated in the "apex" voids located in locally heated region 150 by thermal expansion, and then the rupturing of the membrane 120 propagates along the lines of voids 212 and 214 away from the apex.

More specifically, in the example embodiment of FIG. 2B, when a control voltage is applied to the electrode structure 140, a high thermal density is created in the locally heated region 150 of the membrane 120 as discussed above. The "apex" voids located in the locally heated region 150 are subject to various mechanical stresses, e.g., thermal stress of the membrane material, expansion stress caused by thermal expansion E of the V-shaped electrode 142/144 and tensile stress applied from the internal stress of the membrane 120 (assuming the membrane 120 is formed in pre-stressed state). These mechanical stresses cause an initial rupture in locally heated portion 150 of the membrane 120. Thereafter, the rupturing of the membrane propagates along the lines of the voids 212 and 214 away from the apex by virtue of the thermal expansion force E and/or the tensile stress of the membrane 120. In one embodiment of the invention, the V-shape electrode 142/144 and the linear array of voids 212/214 are formed with an angle in a range of 108° to 120°, which corresponds to hexagonal and pentagonal crack cell structures commonly observed in naturally-occurring fracture patterns. In this regard, the use of an angle in a range of 108° to 120° is believed to provide a mechanism that further facilitates propagation of the crack along the void lines 212 and 214.

In one embodiment of the invention, the voids within the linear arrays of voids 212 and 214 are formed at a pitch roughly twice that of the size of each perforation. The location of the void lines 212/214 can be made as close to the edge of the V-shaped electrode 142/144 as that which can be precisely formed using photolithography and reactive ion etching. For good thermal conduction, it is preferred that the void lines 212/214 are separated from the inner edge of the V-shaped electrode 142/1442 by a distance less than 2 times the thickness of the membrane 120.

Figure 3:
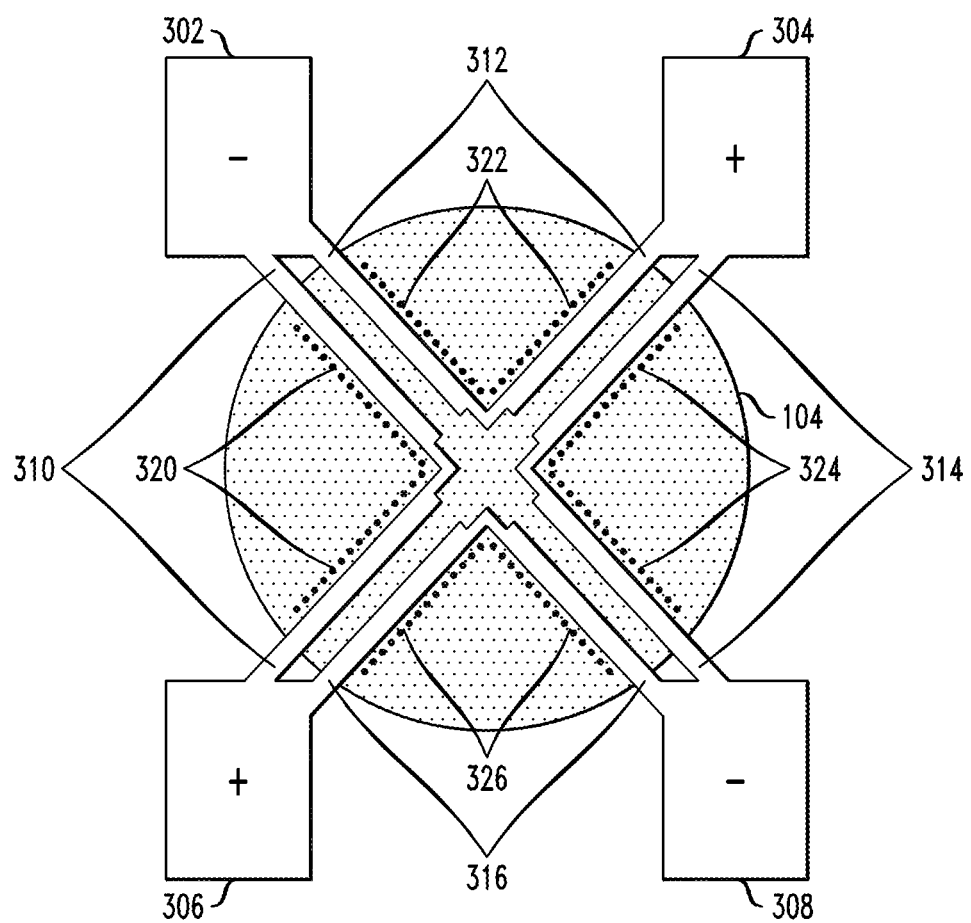
FIG. 3 schematically illustrates a low-power electromechanical release mechanism according to an embodiment of the invention.

FIG. 3 schematically illustrates a low-power electromechanical release mechanism according to an embodiment of the invention. In particular, FIG. 3 illustrates a low-power electromechanical release mechanism 300 comprising an electrode structure including a plurality of anode/cathode contacts 302, 304, 306 and 308, four V-shaped electrodes 310, 312, 314, and 316, and four V-shaped lines of voids 320, 322, 324, and 326 formed in a membrane along the inner edges of the legs the respective V-shaped electrodes 310, 312, 314, and 316. The embodiment of FIG. 3 is conceptually similar in structure and function to the embodiment of FIGS. 2A/2B with regard to the use of a V-shaped electrode and a corresponding V-shaped line of weakness formed by linear arrays of voids. However, the embodiment of FIG. 3 implements a quad-V-shaped electrode structure which enables rupturing of a larger area of the membrane, using the force mechanisms discussed above.

Figure 4:
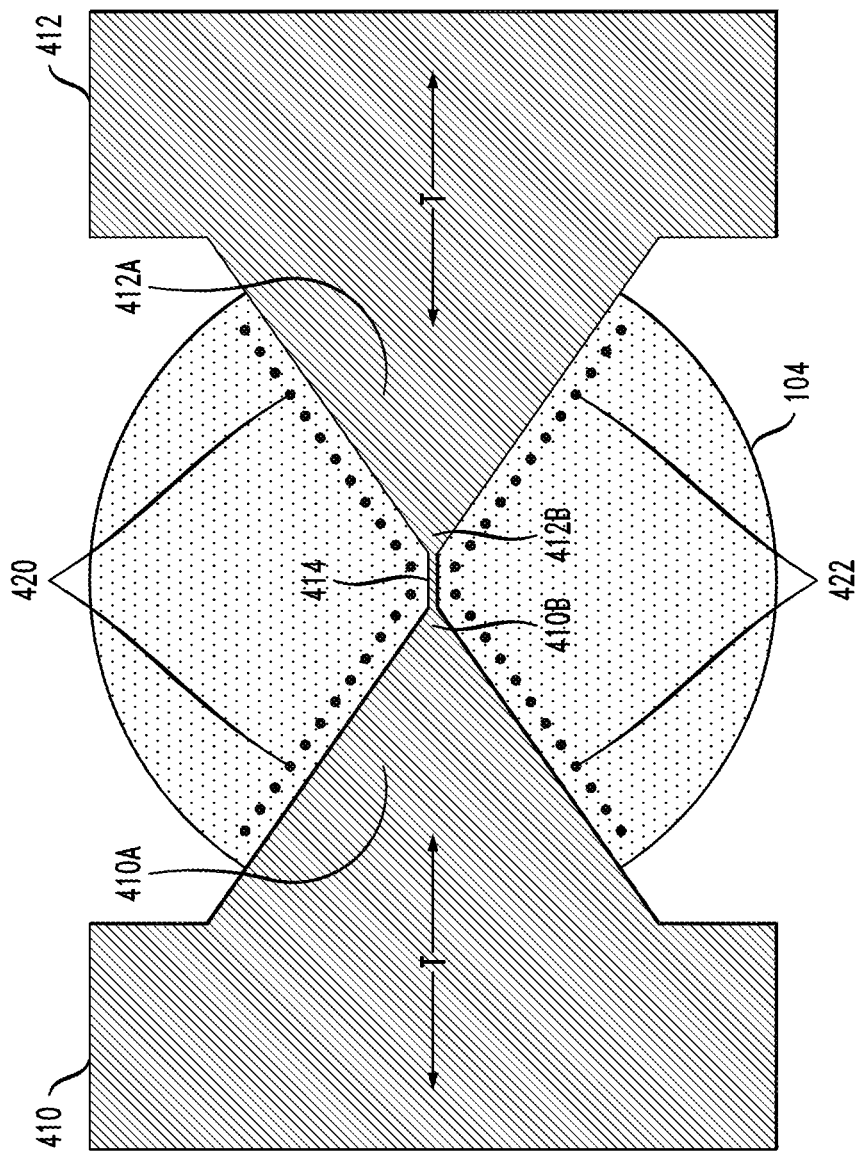
FIG. 4 schematically illustrates a low-power electromechanical release mechanism according to another embodiment of the invention.

FIG. 4 schematically illustrates a low-power electromechanical release mechanism according to another embodiment of the invention. In general, FIG. 4 illustrates a low-power electromechanical release mechanism 400 that is implemented using a stressed electrode structure 410/412/414, according to an embodiment of the invention. The electrode structure 410/412/414 comprises a first electrode 410 and a second electrode 412 and a fuse portion 414 connecting the first and second electrodes 410 and 412. The first and second electrodes 410 and 412 are formed in a tensile-stressed state as indicated by the arrows denoted "T". The low-power electromechanical release mechanism 400 further comprises a plurality of voids 420 and 422 formed within the membrane along one or more edges of the first and second electrodes 410 and 412.

More specifically, in the example embodiment shown in FIG. 4, the first and second electrodes 410 and 412 each comprises a triangular-shaped electrode portion 410A and 412A having a respective apex 410B and 412B. The fuse portion 414 is connected between the apex portions 410B/412B of the first and second electrodes 410/412. Moreover, as shown in FIG. 4, the series of voids 420 form a first V-shaped line of voids that extends adjacent to first edges of the triangular-shaped electrodes 410A and 412A. Similarly, the series of voids 422 form a second V-shaped line of voids that extends adjacent to second edges of the triangular-shaped electrodes 410A and 412A.

When a control voltage is applied to the first and second electrodes 410 and 412, a high current density flows through the fuse portion 414 causing the fuse portion 414 to melt or otherwise break. Moreover, a localized heating of the membrane region surrounding the fuse portion 414, coupled with the existence of voids in the locally heated region of the membrane, collective results in a mechanical stress force that facilitates rupturing of the membrane in the locally heated region of the membrane. Thereafter, the tensile stress present in the first and second electrodes 410 and 412 results in a force that causes the first and second electrodes 410 and 412 to peel back and propagate a rupture in the membrane ling the lines of voids 420 and 422 disposed along the edges of the triangular-shaped electrode portions 410A and 412A.

Figure 5:
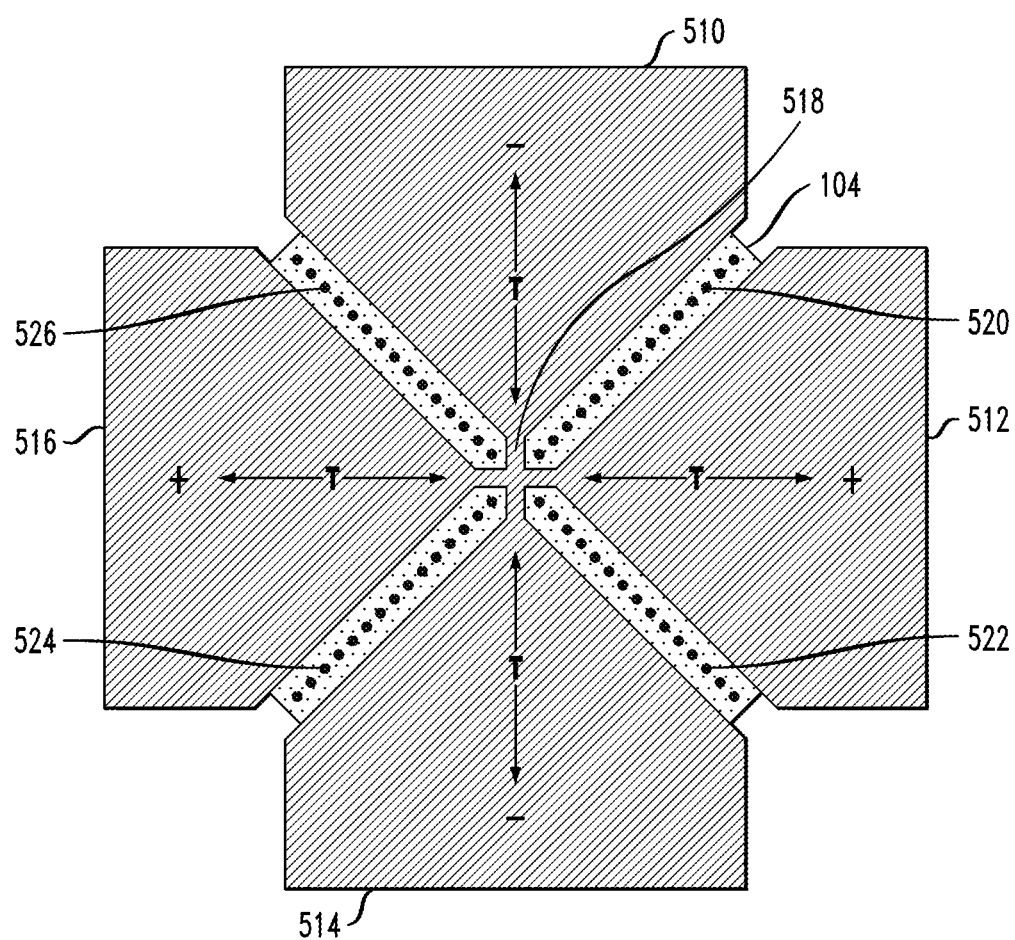
FIG. 5 schematically illustrates a low-power electromechanical release mechanism according to another embodiment of the invention.

FIG. 5 schematically illustrates a low-power electromechanical release mechanism according to another embodiment of the invention. In particular, FIG. 5 illustrates a low-power electromechanical release mechanism 500 which is similar in structure and function to the low-power electromechanical release mechanism 400 of FIG. 4, except that the low-power electromechanical release mechanism 500 of FIG. 5 comprises a stressed electrode structure having first, second, third and fourth triangular-shaped electrodes 510, 512, 514 and 516, which are connected by a fuse portion 518 at apex regions thereof, as shown in FIG. 5. The first, second, third and fourth triangular-shaped electrodes 510, 512, 514 and 516 are formed in a tensile-stressed state as indicated by the respective arrows denoted "T". The low-power electromechanical release mechanism 500 further comprises a line of voids 520, 522, 524 and 526 formed within the membrane between adjacent edges of the first, second, third and fourth triangular-shaped electrodes 510, 512, 514 and 516, as shown in FIG. 5. The embodiment of FIG. 5 implements a quad-electrode structure that enables rupturing of a larger area of the membrane as compared to the embodiment of FIG. 4, while using the force mechanisms discussed above with regard to FIG. 4.

Figure 6:
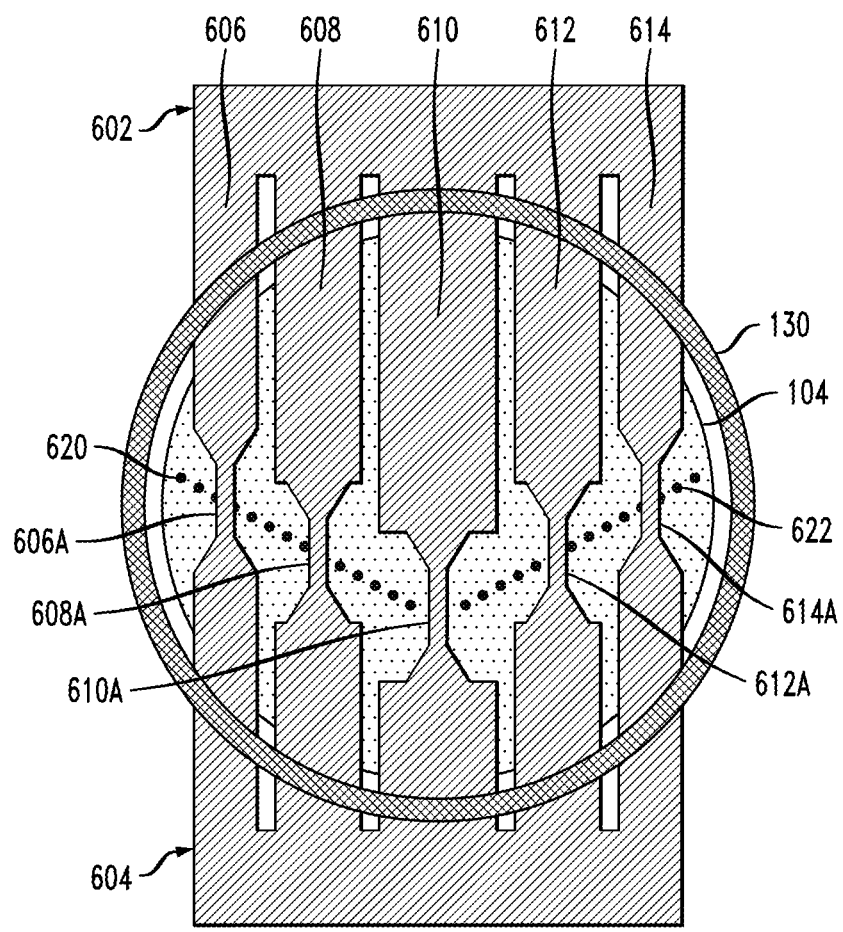
FIG. 6 schematically illustrates a low-power electromechanical release mechanism according to another embodiment of the invention.

FIG. 6 schematically illustrates a low-power electromechanical release mechanism according to another embodiment of the invention. In general, FIG. 6 illustrates a low-power electromechanical release mechanism 600 including an electrode structure comprising a plurality of filaments that are configured to fuse in succession. As shown in FIG. 6, the electrode structure comprises a first contact 602, a second contact 604, and a plurality of filaments 606, 608, 610, 612, and 614 arranged adjacent to each other. The plurality of filaments 606, 608, 610, 612, and 614 are electrically connected in parallel to the first and second contacts 602 and 604 of the electrode structure, wherein the filaments 606, 608, 610, 612, and 614 (or portions thereof) are configured to melt in succession in response to a control voltage applied to the first and second contacts 602 and 604 and cause a rupture in region of the membrane adjacent to the melted portions of the filaments to release contents from within the cavity 104.

In one embodiment of the invention as specifically shown in FIG. 6, the plurality of filaments 606, 608, 610, 612, and 614 include elongated parallel traces, wherein each filament 606, 608, 610, 612, and 614 includes a necked-down portion that converges to a respective fuse portion 606A, 608A, 610A, 612A, and 614A. The fuse portions 606A, 608A, 610A, 612A, and 614A are configured to melt or otherwise break in response to a control voltage applied to the first and second contacts 602 and 604 due to a high current density that flows through the fuse portions 606A, 608A, 610A, 612A, and 614A.

In one embodiment of the invention as shown in FIG. 6, a centrally disposed one of the filaments 610 has a width that is greater than the widths of the other filaments 606, 608, 612 and 614. In addition, the widths of the other filaments 606, 608, 612 and 614 disposed on each side of the centrally disposed filament 610 are made successively smaller. With this configuration, current density is greater in the wider width filaments (less resistance), causing a higher current density in the associated fuse portions. This configuration causes a successive melting of the fuses starting with melting the fuse portion 610A of the centrally disposed filament 610, followed by melting of the fuse portions 608A and 612A of the thinner filaments 608 and 612 disposed on opposite sides of the central filament 610, and then followed by the melting of the fuse portions 606A and 614A of the thinnest filaments 606 and 614.

In one embodiment of the invention, the successive melting of the fuse portions starting from the fuse portion 610A of the central filament 610 causes rupturing of the membrane from the central region of the cavity 104 to the perimeter of the cavity 104. In one embodiment of the invention, the filaments 606, 608, 610, 612 and 614 can be formed in a tensile stressed state such that the breaking of the fuse portions and rupturing of the membrane allows the filaments 606, 608, 610, 612 and 614 to peel back away from the fuse regions and apply a secondary force to assist in rupturing of the membrane.

In another embodiment of the invention, as shown in FIG. 6, the fuse portions 606A, 608A, 610A, 612A, and 614A, of the respective filaments 606, 608, 610, 612, and 614, are arranged along a V-shaped line, wherein a fuse portion of the centrally disposed filament is aligned to an apex of the V-shaped line. In one embodiment of the invention, the V-shaped arrangement of the fuse portions 606A, 608A, 610A, 612A, and 614A is provided along an angle in a range of 108° to 120°, which corresponds to hexagonal and pentagonal crack cell structures that are commonly observed in naturally-occurring fracture patterns. Thus, the angular orientation (in a range of 108° to 120°) of the fuse portions 606A, 608A, 610A, 612A, and 614A can facilitate propagation of the rupture of the membrane along the V-shaped direction.

In yet another embodiment of the invention, to further facilitate rupturing of the membrane, the low-power electromechanical release mechanism 600 of FIG. 6 can further include a plurality of voids 620 and 622 formed within the membrane along the V-shaped line. As shown in FIG. 6, the plurality of voids 620 comprises a line of voids formed in the membrane in alignment to a central region of the fuse portions 606A, 608A, and 610A, and the plurality of voids 622 comprises a line of voids formed in the membrane in alignment to the central region of the fuse portions 610A, 612A and 614A. Again, as noted above, a V-shaped line of voids (e.g., formed by voids 620 and 622) serves to reduce the mechanical strength of the membrane and facilitate the propagation of the rupturing of the membrane as the fuse portions 606A, 608A, 610A, 612A, and 614A successively melt.

Figure 7:
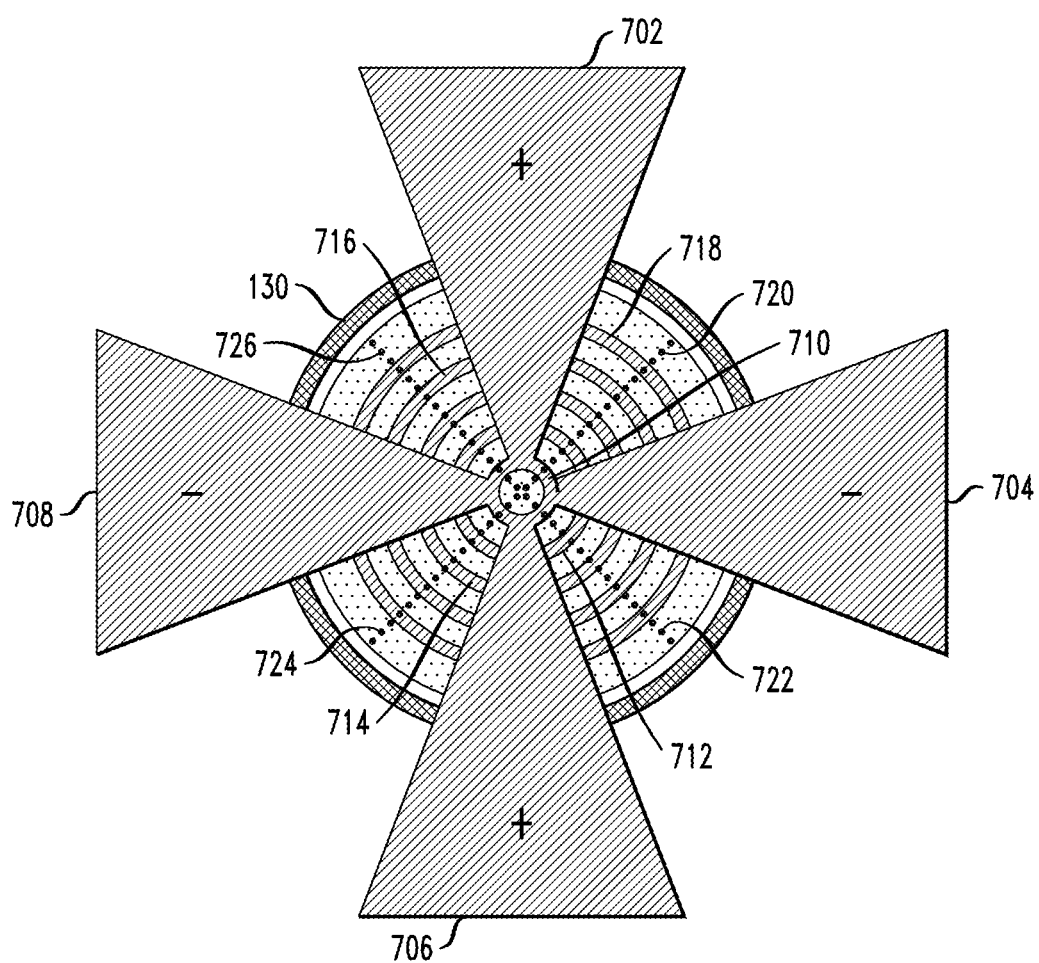
FIG. 7 schematically illustrates a low-power electromechanical release mechanism according to another embodiment of the invention.

FIG. 7 schematically illustrates a low-power electromechanical release mechanism according to another embodiment of the invention. In general, FIG. 7 illustrates a low-power electromechanical release mechanism 700 including an electrode structure comprising a plurality of filaments that are configured to fuse in succession. The release mechanism of the embodiment of FIG. 7 is similar to that discussed above with regard to the embodiment of FIG. 6, except that the embodiment of FIG. 7 implements a circular filament structure. In particular, as shown in FIG. 7, an electrode structure comprises a first contact 702, a second contact 704, a third contact 706, a fourth contact 708 (which are triangular-shaped) and a plurality of circular filament structures 710, 712, 714, 716 and 718 that are concentrically arranged. As shown in FIG. 7, portions (arc segments) of the circular filament structures 710, 712, 714, 716 and 718 are connected between the contacts 702, 704, 706, and 708, wherein in one embodiment of the invention, the electrode structure of FIG. 7 is a planar structure that is patterned on one layer.

In another embodiment of the invention, as shown in FIG. 7, the low-power electromechanical release mechanism 700 includes a plurality of void lines 720, 722, 724 and 726 formed within the membrane along one or more radial lines that radially extend from a center point of the membrane aligned to a center of the innermost circular filament 710.

In operation, when a control voltage is applied to the contacts 702, 704, 706 and 708 (with the polarities as shown), a high current density is initially created at a central region of the electrode structure, causes the innermost circular filament 710 to melt and begin the rupturing of the membrane due to various mechanical stress mechanisms as discussed herein. Thereafter, the current density is distributed to successively melt the portions of the circular filaments 712, 714, 716, and 718, disposed between the contacts 702, 704, 706 and 708. In an embodiment in which the radial void lines 720, 722, 724, and 726 are implemented, rupturing of the membrane is propagated along the defined radial lines as the circular fuse portions 710, 712, 714, 716 and 718 successively melt.

Figure 8B:
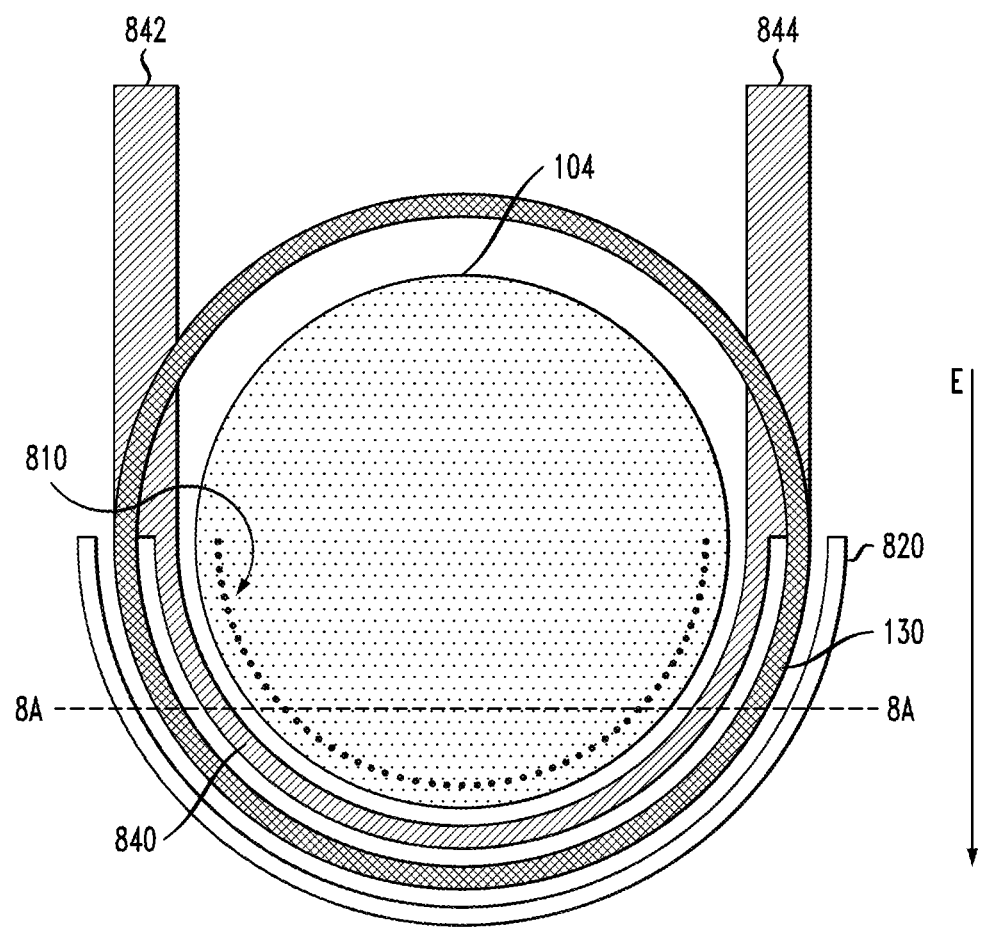

FIGS. 8A and 8B schematically illustrate a microchip substance delivery device having a low-power electromechanical release mechanism, according to another embodiment of the invention. FIG. 8B is a schematic top plan view showing portions of the device 800 and FIG. 8A is a schematic side view of the device 800 along line 8A-8A in FIG. 8B. Collectively, FIGS. 8A and 8B illustrate a microchip substance delivery device 800 which is similar to the device 200 of FIGS. 2A and 2B, except that the device 800 comprises a circular array of voids (or perforations) 810 formed in the membrane 120, a groove 820 formed in the membrane 120, and a circular electrode 840, all which service to facilitate rupturing of the membrane 120 using mechanical stress mechanisms as discussed herein.

As specifically shown in FIG. 8B, an electrode structure comprises first and second contacts 842 and 844 which are connected to ends of the circular electrode 840. The circular groove 820 as shown in FIG. 8B serves to partially terminate the membrane 120 outside the region of the cavity 104. In other words, the groove 820 serves to locally isolate a portion of the membrane 120 around the periphery of the cavity, or otherwise segment a portion of the membrane periphery. In this way, the membrane 120 can either be fully or partially released from the cavity 104, without rupturing the membrane itself, and without creating debris ejected from the device. The groove 820 also provides a gap for thermal expansion of the surface region of the membrane 120, as desired in an embodiment where the membrane 120 is to be ruptured.

In particular, in the embodiment of FIG. 8B, the circular electrode 840 has a width that is smaller than a width of the first and second contacts 842 and 844. In this manner, as discussed above, the circular electrode 840 provides localized heating or a portion of the membrane 120 that is in proximity to the circular electrode 840, wherein the local heating causes mechanical stress in the locally heated region of the membrane 120. Moreover, the circular line of voids 810 is formed in the membrane 120 adjacent to an inner edge of the circular electrode 840 to provide a line of mechanical weakness in the locally heated region of the membrane 120, which further facilitates the rupturing of the locally heated portion of the membrane, and in particular, along the line of weakness provided by the circular line of voids 810.

Furthermore, the mechanical force E that is exerted on the membrane 120 due to the thermal expansion of the electrode structure 840/842/844 further facilitates rupturing of the membrane 120 along the line of weakness provided by the circular line of voids 810 in the locally heated region of the membrane. The groove 820 formed in the membrane 120 provides a gap that allows the membrane 120 to be stretched in the direction of the thermal expansion (indicated by the arrow E) to facilitate the rupturing of the membrane along the circular line of voids 810.

In other embodiments of the invention, low-power electromechanical release mechanisms are configured to melt or otherwise rupture the seal (as opposed to the membrane) to release the contents of the cavities. Example embodiments of release mechanisms that are based on melting or breaking a seal will now be discussed with reference to FIGS. 9, 10, 11 and 12A/12B.

Figure 9:
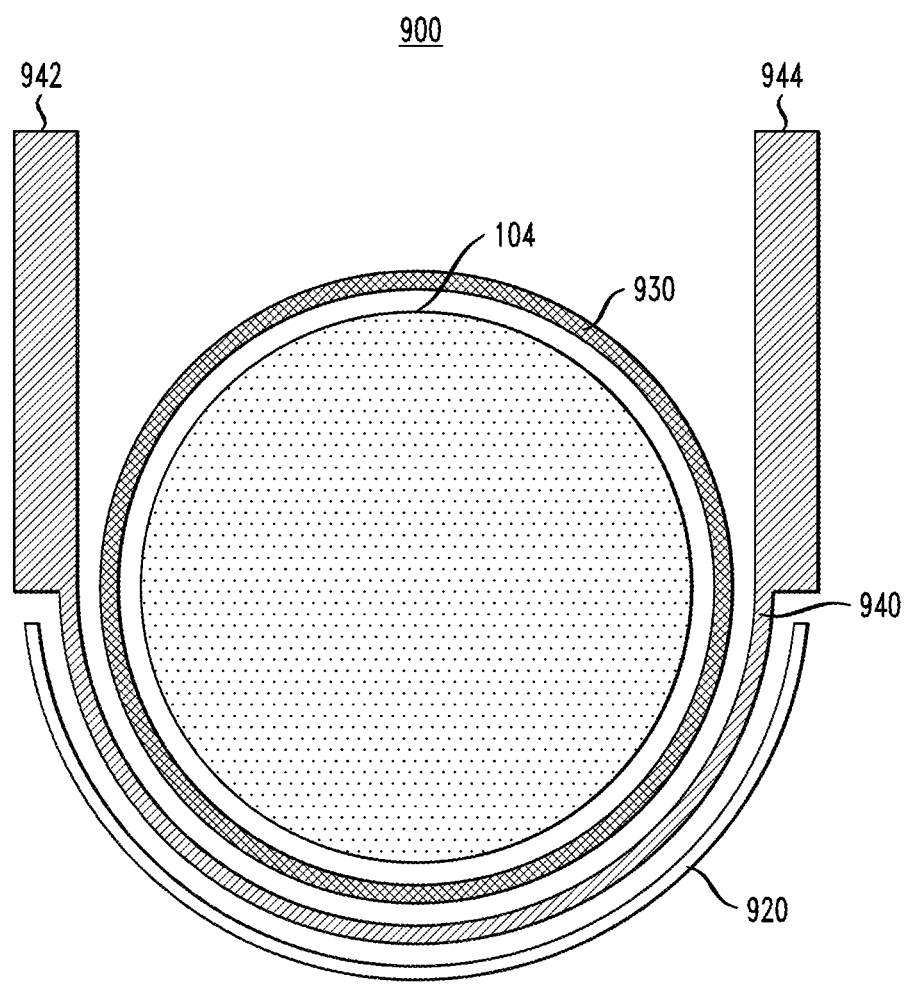
FIG. 9 schematically illustrates a low-power electromechanical release mechanism according to another embodiment of the invention.

FIG. 9 schematically illustrates a low-power electromechanical release mechanism which is configured to melt a seal, according to another embodiment of the invention. In general, FIG. 9 illustrates a low-power electromechanical release mechanism 900 comprising a seal 930 that is disposed between a membrane and the surface of a substrate, wherein the seal 930 surrounds the opening of a cavity 104, and wherein the seal 930 and membrane are configured to enclose the cavity 104 and retain a substance within the cavity 104, similar to previous embodiments discussed above. An electrode structure 940/942/944 is configured to locally heat a least a portion of the seal 930 in response to a control voltage applied to the electrode structure, and melt the locally heated portion of the seal 930 to release the substance from within the cavity 104. The seal 930 may be formed of a low melting point metallic material (such as indium) or a non-metallic material (e.g., polymer).

More specifically, in the embodiment of FIG. 9, a portion of the electrode structure includes a semi-circular electrode 940 having a width that is smaller than a width of first and second contacts 942 and 944. Moreover, the semi-circular electrode 940 is disposed adjacent to a portion of the seal 930. In this manner, as discussed above, the semi-circular electrode 940 provides localized heating in a region of the membrane that is in proximity (adjacent) to a portion of the seal 930, which thereby causes localized heating of a portion of the seal 930 which is in proximity to the semi-circular electrode 940. This local heating causes a portion of the seal 930 to melt and thereby decouple a portion of the membrane from the substrate. In this embodiment, the circular groove 920 formed in the membrane allows a portion of the membrane (which is released by the melting of the seal) to freely move upward (e.g., fold upward) thereby release contents of the cavity 104. The membrane can have one or more layers formed a pre-stressed state to facilitate a "peel back" of the released portion of the membrane from the groove 920.

In another embodiment of the invention, the low-power electromechanical release mechanism 900 of FIG. 9 can be configured such that portions of both the seal 930 and the circular electrode 940 melt in response to the control voltage applied to the electrode structure.

Figure 10:
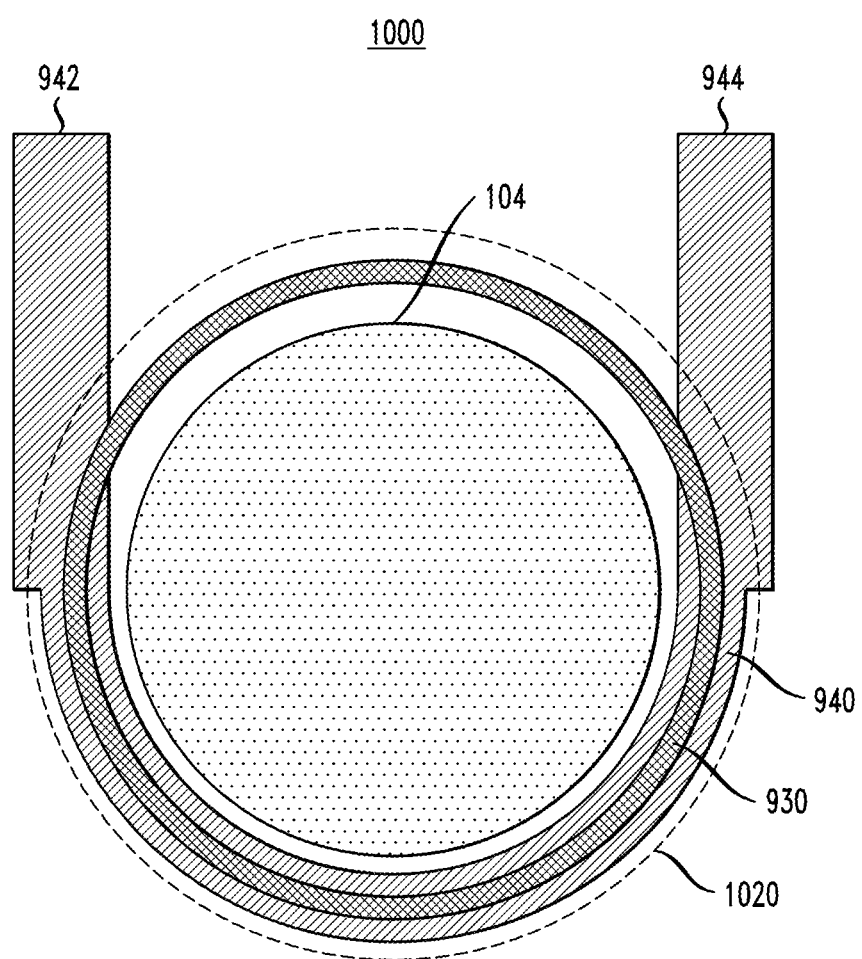
FIG. 10 schematically illustrates a low-power electromechanical release mechanism according to another embodiment of the invention.

FIG. 10 schematically illustrates a low-power electromechanical release mechanism which is configured to melt a seal, according to another embodiment of the invention. In general, FIG. 10 illustrates a low-power electromechanical release mechanism 1000 which is similar to the embodiment of FIG. 9, expect that a portion of the seal 930 is disposed on a layer above (or below) the semi-circular circular electrode 940. Furthermore, in the embodiment of FIG. 10, a circular groove 1020 is formed to fully isolate the membrane structure of the given cavity 104 and allow the membrane structure to become fully disconnected from the seal 930 upon melting a portion of the seal 930 by virtue of the localized heating generated by the semi-circular electrode 940 that overlaps the target portion of the seal 930. With this embodiment, complete removal of the membrane over the cavity 104 allows rapid and full release of the contents of the cavity 104. In such embodiment, each cavity is formed with a separate membrane structure.

Figure 11:
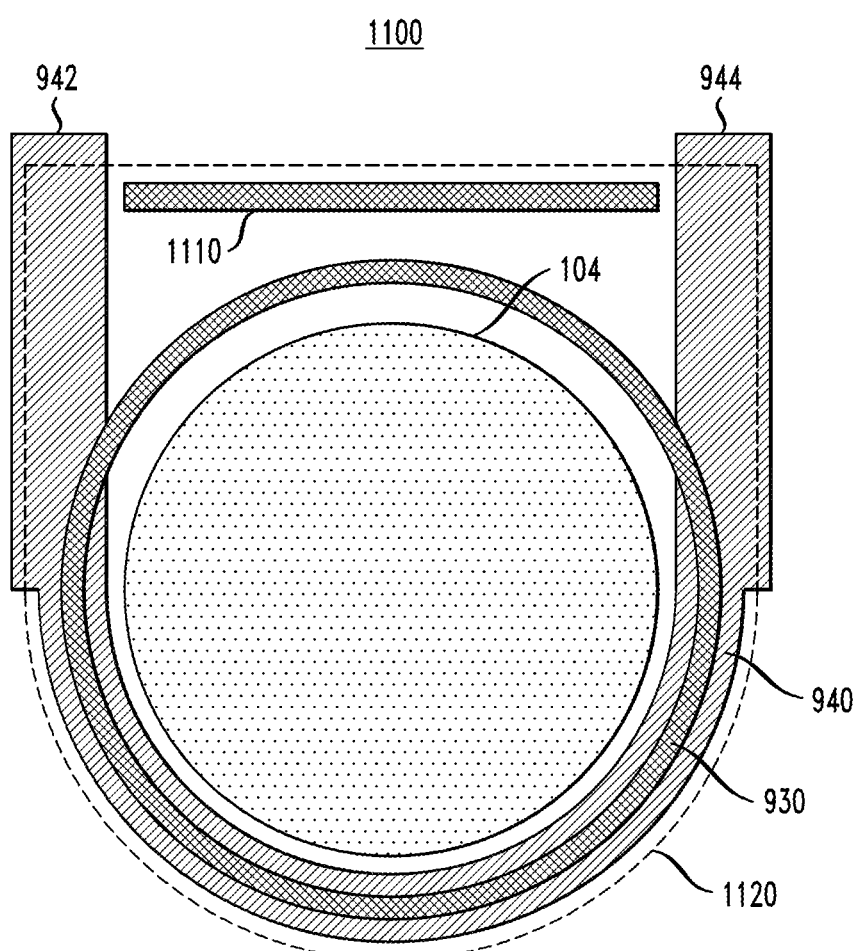
FIG. 11 schematically illustrates a low-power electromechanical release mechanism according to another embodiment of the invention.

FIG. 11 schematically illustrates a low-power electromechanical release mechanism which is configured to melt a seal, according to another embodiment of the invention. In general, FIG. 11 illustrates a low-power electromechanical release mechanism 1100 which is similar to the embodiment of FIG. 10, expect for the use of a hinge structure 1110 that is connected to one end of an isolated membrane 1020. This structural configuration allows the isolated membrane 1020 to operate as a hinged lid that hingedly opens upon melting of a portion of the seal 930 due to the local heating thereof by the semi-circular electrode 940. The hinge structure 1110 can be formed of the same material that is used to form the seal 930. With this embodiment, the isolated membrane 1120 covering the cavity 104 can be fully opened to allow the rapid and full release of the contents of the cavity 104, without completely disconnecting the isolated membrane 1120 from the microchip substance delivery device.

Figure 12A:
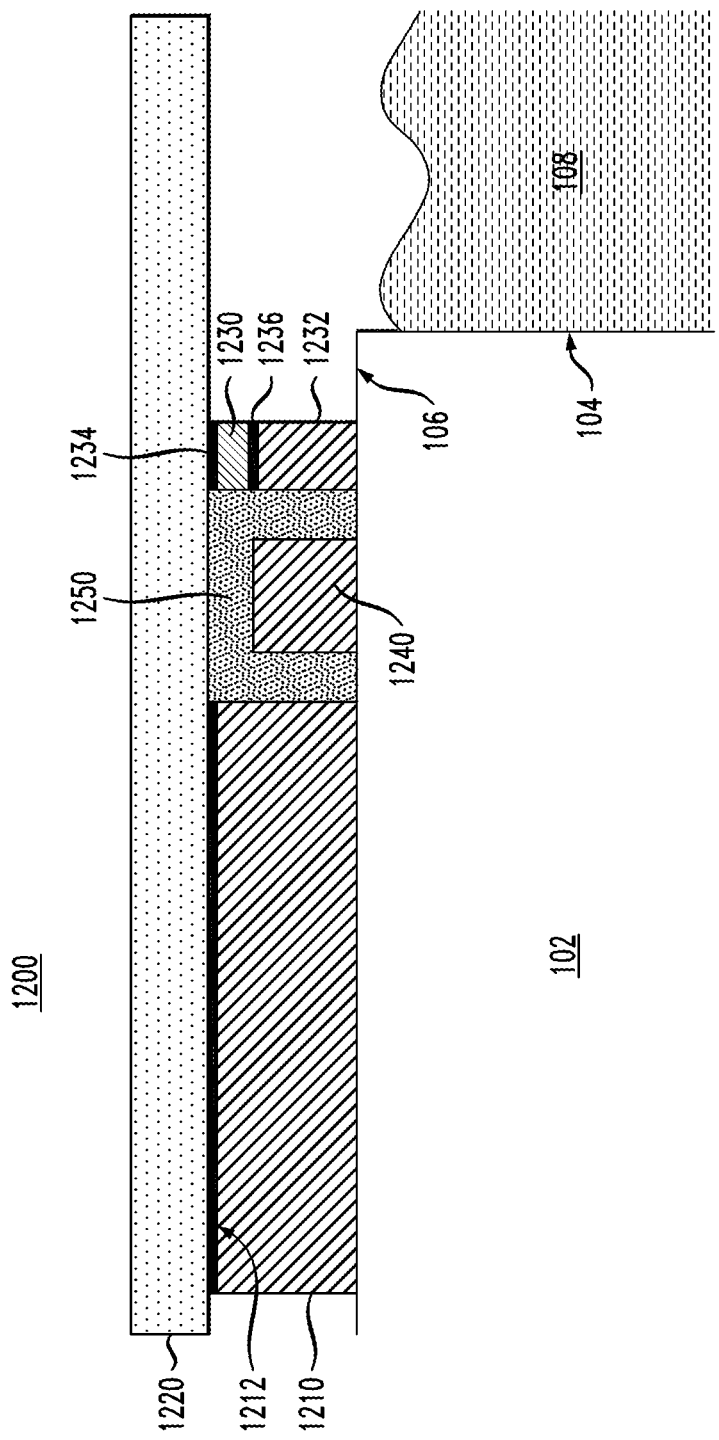
FIGS. 12A and 12B schematically illustrate a microchip substance delivery device having a low-power electromechanical release mechanism, according to another embodiment of the invention.
Figure 12B:
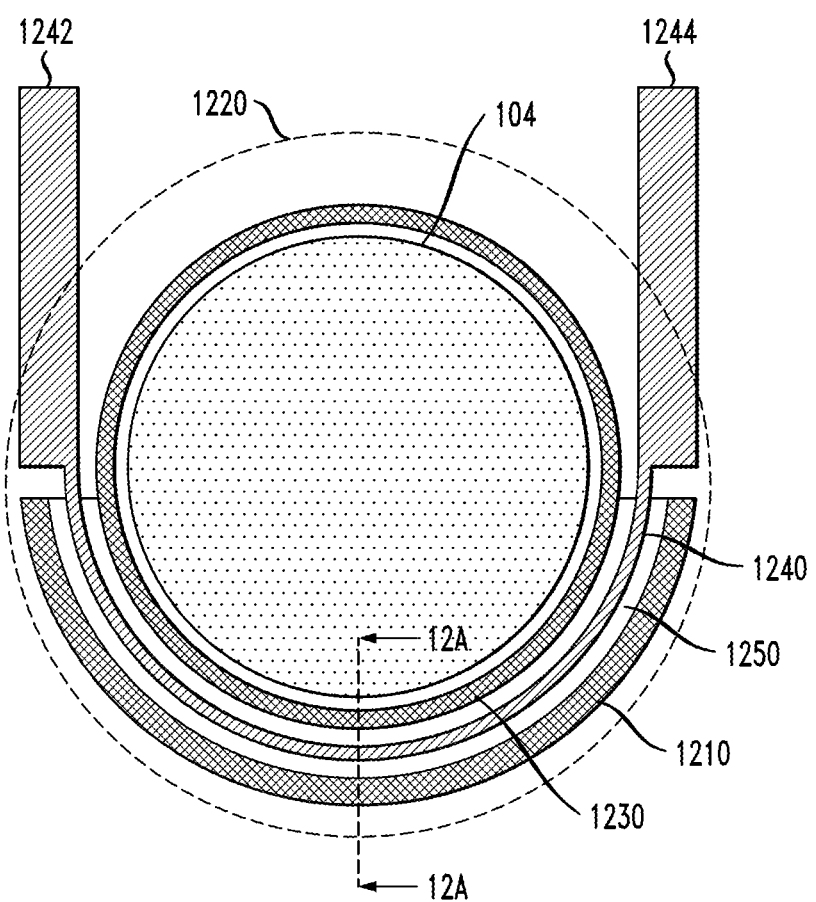

FIGS. 12A and 12B schematically illustrate a microchip substance delivery device 1200 having a low-power electromechanical release mechanism which is configured to break a seal, according to another embodiment of the invention. FIG. 12A is a partial cross-sectional view of the microchip substance delivery device 1200 along line 12A-12A in FIG. 12B. Referring collectively to FIGS. 12A and 12B, a microchip substance delivery device 1200 comprises a substrate 102 comprising a cavity 104 formed in a surface 106 of the substrate 102. A membrane 1220 is disposed on the substrate 102 covering an opening of the cavity 104. In one embodiment, the membrane 1220 comprises a layer of insulating or polymer material that is formed in stressed state. As shown in FIG. 12B, the membrane 1220 is an isolated structure (i.e., not connected or otherwise integrally formed with membranes of other cavities).

The microchip substance delivery device 1200 further comprises a mechanical stop 1210 (or pedestal) formed on the surface 106 of the substrate 102 and disposed along a portion of an outer perimeter region of the membrane 1220. In one embodiment, the mechanical stop 1210 is coupled to the membrane 1120 using an interface material layer 1212. Furthermore, a seal 1230 and pedestal structure 1232 are formed on the surface 106 of the substrate 102 in proximity to, and surrounding the cavity 104. The seal 1230 is bonded to the membrane 1220 and the pedestal structure 1232 using interface material layers 1234 and 1236, respectively. As with previously discussed embodiments, the seal 1230 and membrane 1220 configured to enclose the cavity 104 and retain a substance 108 within the cavity 104.

In one embodiment, the mechanical stop 1210 and pedestal 1232 structures are formed of metallic materials such as copper, nickel or aluminum, for example. In another embodiment, the mechanical stop 1210 and pedestal 1232 structures are formed of polymer materials (e.g., epoxy, plastic, photopolymer, etc.). In one embodiment of the invention, the interface material layer 1212 is formed of a low adhesive material such as a polymer or Teflon or a weakly adhering material such as Rh or Zn. Further, in one embodiment of the invention, the interface material layers 1234 and 1236 are formed of metallic materials such as Ni, CuNi, NiFe, Al, etc. The seal layer 1230 can be formed of a metallic material such as In or Sn or an alloy comprising In and other metallic material.

The microchip substance delivery device 1200 further comprises an electrode structure 1240/1242/1244 comprising first and second contacts 1242 and 1244, and a semi-circular electrode 1240 formed on the surface 106 of the substrate 102 between the mechanical stop 1210 and the pedestal 1232. A low-adhesion polymer material 1250 encapsulates the semi-circular electrode 1240. In one embodiment, the low-adhesion polymer material 1250 comprises volatile elements such as water, alcohol or other organic materials.

In general, the embodiment of FIGS. 12A/12B provides a release mechanism which involves breaking the interface between the seal 1230 and the membrane 1120 and/or pedestal 1232, and breaking the interface between the mechanical stop 1210 and the membrane 1220, based on a localized heating local. In particular, the semi-circular electrode 1240 is configured to locally heat a proximate region surrounding the semi-circular electrode 1240 in response to a control voltage applied to the first and second contacts 1242 and 1244 of the electrode structure.

In one embodiment of the invention, this localized heating results in a thermal expansion of the materials in the region surrounding the semi-circular electrode 1240, in particular, a thermal expansion portion of the membrane 1220 disposed in proximity to the semi-circular electrode 1240. Such thermal expansion results in the generation of mechanical shear stresses that are exerted on the seal 1230 and the interface layers 1212, 1234 and 1236. The interface layers 1212, 1234 and 1236 are configured to mechanically fail and break as a result of the mechanical shear stress, and thereby effectively to break at least a portion of the seal 1230 in proximity to the semi-circular electrode 1240 and release the substance 108 from within the cavity 104.

In another embodiment of the invention, when the low-adhesion polymer material 1250 is formed with volatile components, the polymer material 1250 is configured to release the volatile components in response to the localized heating of the polymer material 1250 by the semi-circular electrode 1240. The release of the volatile components from the polymer material 1250 causes an increase in pressure in the encapsulated region surrounding the semi-circular electrode 1240, which generates a force that is sufficient to break the interface layers 1234 and/or 1236.

In the embodiment shown in FIGS. 12A/12B, the mechanical stop 1210 has a lateral dimension that is larger than the lateral dimensions of the pedestal and seal structures 1232 and 1230, and the interface layer 1212 is configured to provide a low adhesion interface between the mechanical stop 1210 and the membrane 1220. However, because of the large lateral size of the mechanical stop 1210, the conduction path for the escaping gas (released volatile components) is smaller through the seal interfaces 1234 and 1236, as opposed to the interface 1212 between the mechanical stop 1210 and the membrane 1220. Therefore, in one embodiment of the invention, the force that is generated as a result of the escaping gas is sufficient to apply a shear stress to break one or both of seal interface layers 1234 and 1236. Following the shearing through one or both of the seal interface layers 1234 and 1236, the membrane 1220 will exert a force on the interface layer 1212 and cause the membrane 1220 to break away from the mechanical stop 1210, thereby allowing the substance 108 to be released from the cavity 104 through the broken interface layers 1212 and 1234/1236. The force that is exerted on the interface 1212 by the membrane 1220 is generated by virtue of the pre-stressed state of the membrane 1220, the thermal expansion of the membrane 1220, or both.

Figure 13A:
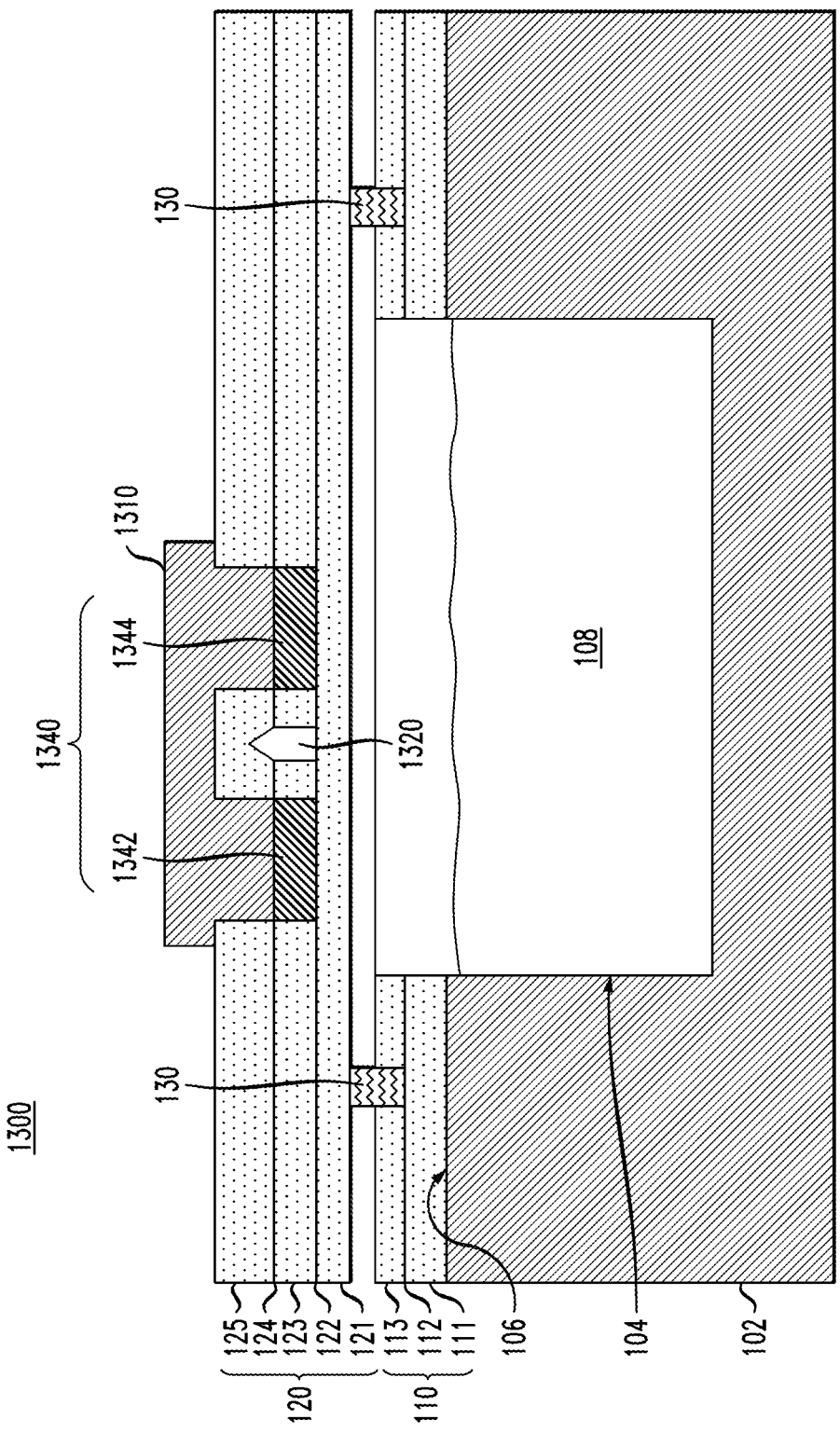
FIGS. 13A and 13B schematically illustrate a microchip substance delivery device having a low-power electromechanical release mechanism, according to another embodiment of the invention.
Figure 13B:
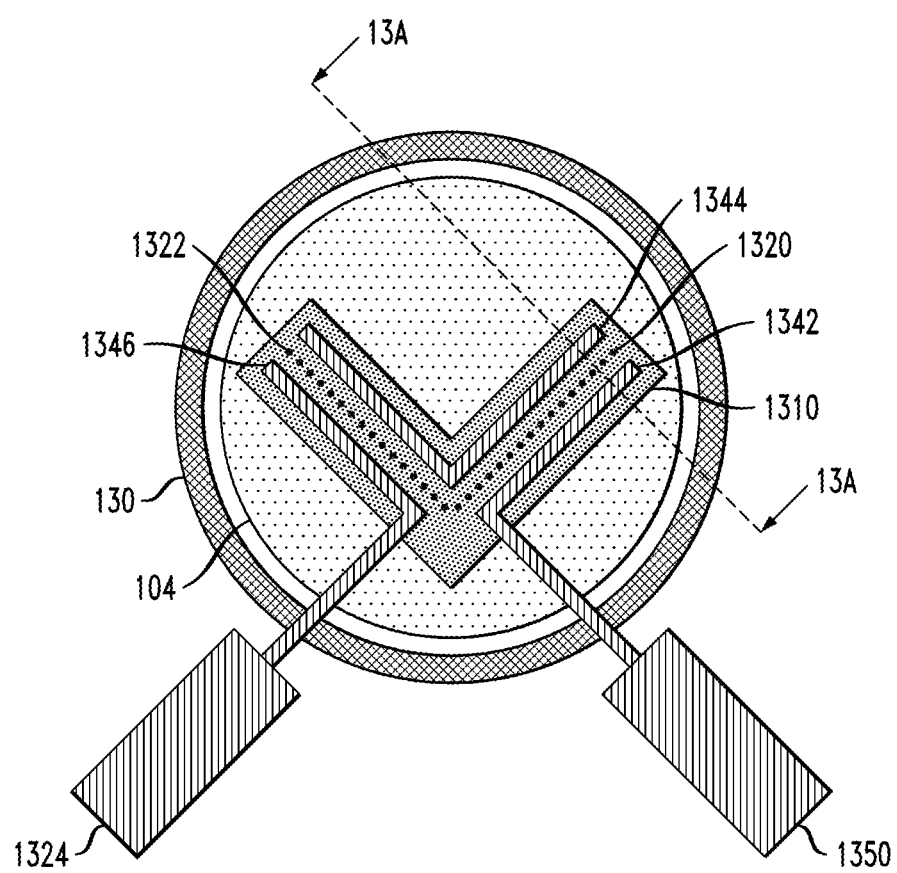

FIGS. 13A and 13B schematically illustrate a microchip substance delivery device having a low-power electromechanical release mechanism, according to another embodiment of the invention. In general, FIGS. 13A and 13B schematically illustrate a microchip substance delivery device 1300 which is similar to the embodiments of the devices 100 and 200 discussed above, except that the device 1300 comprises a composite metallic and non-metallic membrane, wherein a locally heated portion of the membrane comprises a metallic material that is configured to melt due to the localized heating thereof. In particular, referring collectively to FIGS. 13A and 13B (where FIG. 13A is a cross section of the device 1300 taken along line 13A-13A in FIG. 13B), the device 1300 comprises a membrane 120 comprising a plurality of insulating layers 121, 122, 123, 124 and 125 (e.g., silicon dioxide and silicon nitride layers as discussed above), was well as a metallic membrane structure 1310 that is electrically coupled to an electrode structure 1340. Moreover, a plurality voids 1320 are formed in the insulating material of the membrane 120 underneath the metallic membrane structure.

As more specifically shown in FIG. 13B, the electrode structure 1340 comprises a first V-shaped element 1342, a second V-shaped element 1344 and a third V-shaped element 1346. The second V-shaped element 1344 is electrically connected to the first and third V-shaped elements 1342 and 1346 via the metallic membrane structure 1310 (shown in phantom in FIG. 13B). The electrode structure 1340 further comprises first and second contacts 1348 and 1350 which serve as anode/cathode contacts to receive a control voltage. The device 1230 further comprises a V-shaped array of voids 1320/1322 comprising a first line of voids 1320 and a second line of voids 1322. The first line of voids 1320 is formed in the insulating material layers in a region of the membrane 120 disposed between portions of the first and second V-shaped electrode elements 1342 and 1344. Similarly, the second line of voids 1322 is formed in the insulating material layers in a region of the membrane 120 disposed between portions of the second and third V-shaped electrode elements 1344 and 1346.

In the embodiment of FIGS. 13A and 13B, the metallic membrane structure 1310 is formed of a low-melting point metallic material which is configured to serve as fuse structure that melts (or partially melts) in response to a high density current that flows through the metallic membrane structure between the first and third V-shaped electrode element 1342 and 1346 and the second V-shaped electrode element 1344. As the current flows, the electrode structure locally heats a portion of the insulating membrane 120 comprising the void lines 1320 and 1322, which imparts a mechanical stress in the locally heated region of the insulating membrane 120, and causes propagation of the membrane rupturing along the void lines 1320 and 1322. The melting of the metallic membrane element 1310 and the weakening of the membrane 120 due to thermal stress in the locally heated region results in the rupturing of the membrane along the void lines 1320 and 1322 based on similar mechanical force mechanisms as discussed herein.

In another embodiment of the invention, the metallic membrane structure 1310 is formed of a highly stressed metallic material that is configured to crack as a result of additional mechanical stress applied to the metallic membrane structure 1310 when heated due to current flowing through the metallic membrane structure 1310. In this embodiment, the mechanical cracking of the metallic membrane structure 1310, coupled with the mechanical cracking of the portion of the membrane in which the voids 1320 and 1322 are formed, provides an effective actuation mechanism to mechanically rupture the membrane 120 in the region between the electrodes 1342, 1344, 1346, without necessarily melting the metallic membrane structure 1310.

Figure 14A:
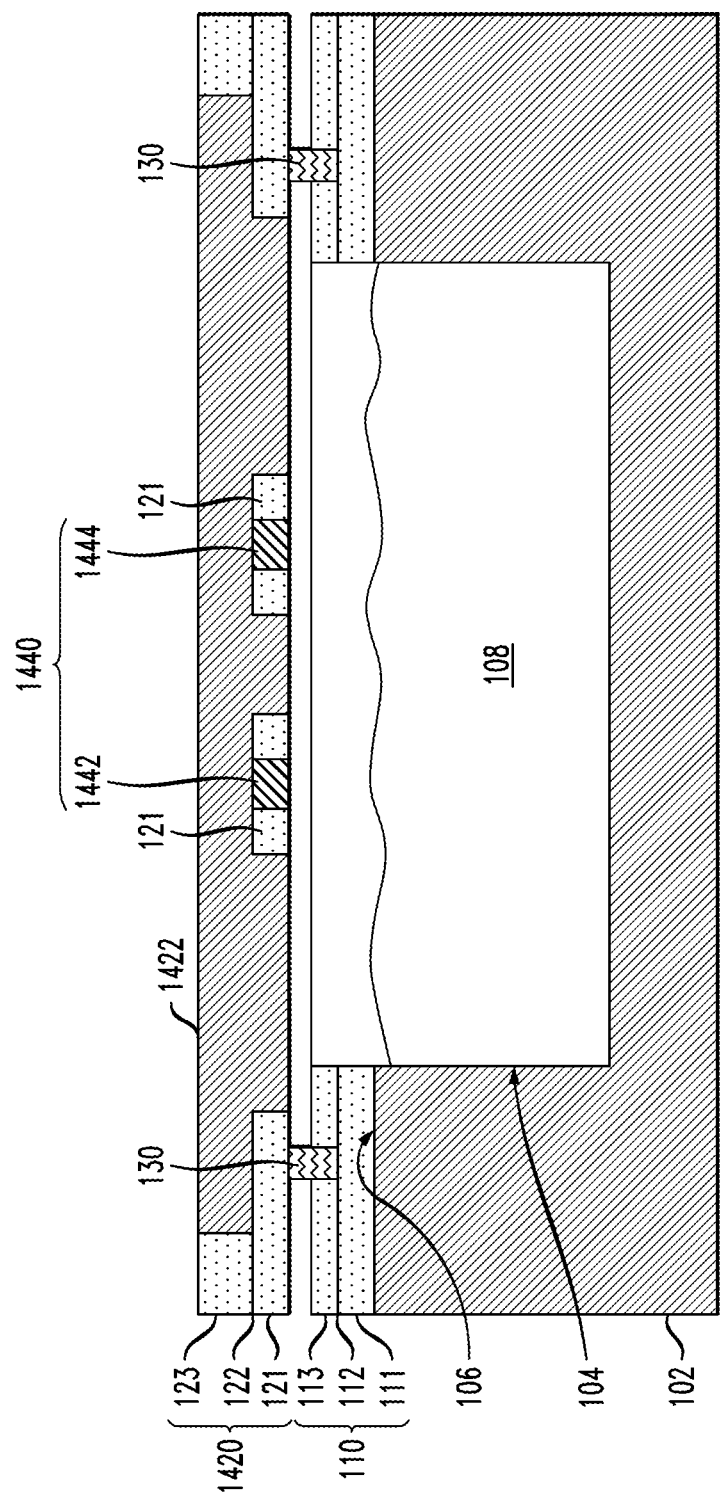
FIGS. 14A and 14B schematically illustrate a microchip substance delivery device having a low-power electromechanical release mechanism, according to another embodiment of the invention.
Figure 14B:
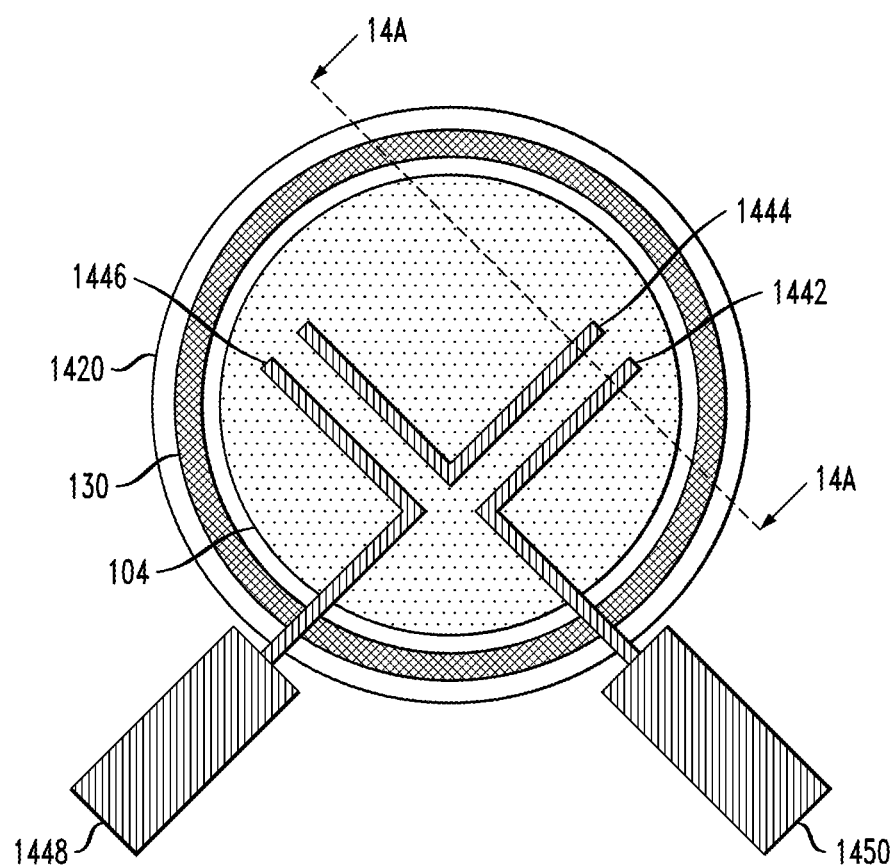

FIGS. 14A and 14B schematically illustrate a microchip substance delivery device having a low-power electromechanical release mechanism, according to another embodiment of the invention. In general, FIGS. 14A and 14B schematically illustrate a microchip substance delivery device 1400 which is similar to the embodiments of the devices 100 and 200 discussed above, except that the device 1400 comprises a metallic membrane, wherein an electrode structure is configured to locally heat and melt a portion of the metallic membrane. In particular, referring collectively to FIGS. 14A and 14B (where FIG. 14A is a cross section of the device 1400 taken along line 14A-14A in FIG. 14B), the device 1400 comprises a membrane 1420 comprising a plurality of insulating layers, e.g., silicon dioxide layer 121, silicon nitride layer 122 and silicon dioxide layer 123, and a metallic membrane 1422 that is electrically coupled to an electrode structure 1440. In the embodiment of FIGS. 14A and 14B, the membrane structure 1420 is a separate structure that is isolated from other membranes for over cavities formed on the device 1400.

As more specifically shown in FIG. 14B, the electrode structure 1440 comprises a first V-shaped element 1442, a second V-shaped element 1444 and a third V-shaped element 1446, which are electrically coupled to each other through the metallic membrane 1422 layer. The electrode structure 1440 further comprises first and second contacts 1448 and 1450 which serve as anode/cathode contacts to receive a control voltage. In one embodiment of the invention, the metallic membrane structure 1422 is formed of a low-melting point metallic material which is configured to melt (or partially melt) in response to high density current flow that flows through the metallic membrane structure 1422 between the first, second and third V-shaped electrode elements 1442, 1444, and 1446. As shown in FIG. 14A, a portion of the silicon dioxide layer 121 is disposed adjacent to the sidewalls of the V-shaped electrode structures 1442 and 1422 and 1446, so that the current flow is restricted to a region of the metallic membrane 1422 above and between the V-shaped electrode elements 1442, 1444, and 1446.

Figure 15:
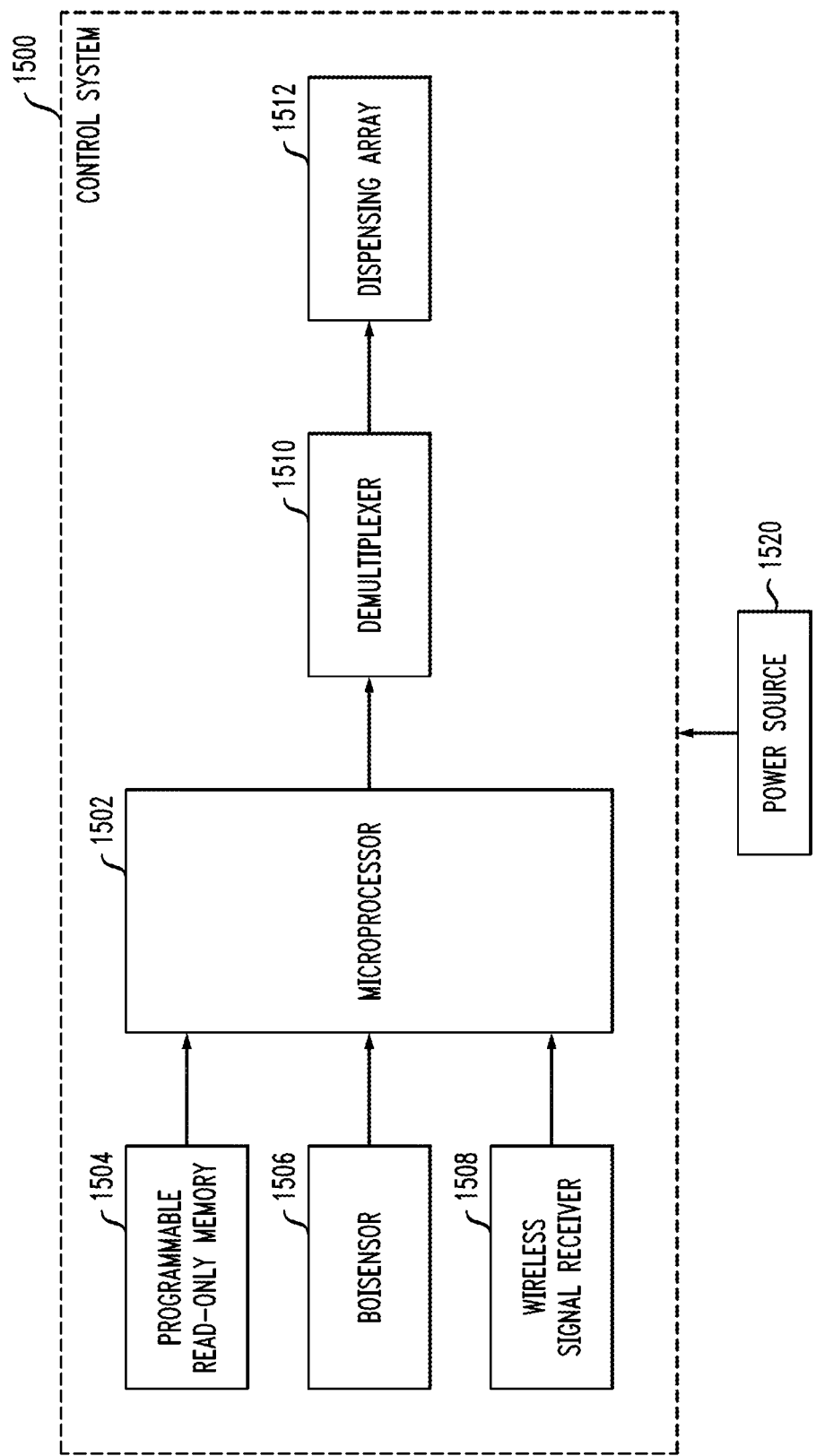
FIG. 15 is a block diagram of control circuitry that is configured to control the release of reservoir contents of a microchip substance delivery device, according to an embodiment of the invention.

FIG. 15 is a block diagram of control circuitry that is configured to control the release of reservoir contents of a microchip substance delivery device, according to an embodiment of the invention. In particular, FIG. 15 illustrates a control system 1500 coupled to a power source 1520. In general, the control system 1500 comprises a microprocessor 1502, a programmable ROM 1504, one or more biosensors 1506, a wireless receiver 1508, a demultiplexer circuit 1510 and a dispensing array 1512. Various components of the control system 1500 include integrated circuits that is integrally formed as part of a microchip in which low-power electromechanical release structures and content filled cavities are formed according to embodiments of the invention as described above. In FIG. 15, the dispensing array 1512 generically represents the various low-power releasable membrane structures and cavity arrays as discussed above. The control system 1500 can be designed using standard circuit design methods and built with standard silicon integrated circuit technology.

The microprocessor 1502 generates control signals to the demultiplexer circuitry 1520 to selectively activate one or more releasable membrane structures of the dispensing array 1512. The microprocessor 1502 can generate control signals to activate substance release according to a programmed scheduled stored in the programmable ROM 1504. In another embodiment, the microprocessor 1502 can generate control signals to activate substance release according to control signals output from one or more biosensors 1506 which automatically detect when doses of a given drug or medication are to be administered via activation of one or more releasable membrane structures. In yet another embodiment, the microprocessor 1502 can generate control signals to activate substance release according to control signals output from a wireless receiver based on remote commands provided by the doctor or individual using or controlling the microchip substance delivery device.

In one embodiment of the invention, the power source 1520 can be implemented as an internal power source, such as a bio-compatible thin-film battery, that is integrated with the microchip substance delivery device. For this application, battery size, material, and packaging requirements limit the energy capacity, and it is for this reason that the energy requirements for substrate release are preferably minimized using low-power electromechanical release mechanisms according to embodiments of the invention. In other embodiments, the power source 1520 can be implemented as a wireless power delivery system in which the power is transmitted to the control system 1500 from an external source.

It is to be understood that electromechanical substance delivery devices described herein can be utilized in various types of drug delivery applications. For example, an electromechanical substance delivery device can be positioned in a target location within an individual's body by implantation (e.g., under skin, near tear duct, etc.). Implantation is beneficial when the electromechanical substance delivery device is to remain within the body to administer multiple doses of drugs/medications over a relatively long period of time. In other applications, an electromechanical substance delivery device can be implemented as part of an ingestible device (e.g., swallowable pill) which can be swallowed by an individual. In this application, drug delivery can be provided over a shorter time period that it takes for the ingestible device to pass through the individual's digestive tract. Moreover, in other applications, an electromechanical substance delivery device can be implemented as a wearable device (e.g., a transdermal device or a component of a transdermal device) that is configured to deliver drugs through an individual's skin.

Although embodiments have been described herein with reference to the accompanying drawings for purposes of illustration, it is to be understood that the present invention is not limited to those precise embodiments, and that various other changes and modifications may be affected herein by one skilled in the art without departing from the scope of the invention.

We claim:

1. An electromechanical device, comprising:
   a substrate comprising a cavity formed in a surface of the substrate;
   a membrane disposed over the surface of the substrate and covering an opening of the cavity, wherein the membrane comprises a stack of insulating layers comprising at least a first insulating layer and a second insulating layer;
   a seal disposed between the membrane and the surface of the substrate, wherein the seal surrounds the opening of the cavity, and wherein the seal and the membrane are configured to enclose the cavity and retain a substance within the cavity; and
   an electrode structure embedded within the stack of insulating layers of the membrane with the electrode structure disposed between the first and second insulating layers of the membrane;
   wherein a surface area of a portion of the electrode structure that is disposed over the opening of the cavity is less than a surface area of the opening of the cavity; and
   wherein the electrode structure is configured to locally heat a portion of the stack of insulating layers of the membrane in response to a control voltage applied to the electrode structure, and create a mechanical stress that causes a rupture in the locally heated portion of the stack of insulating layers of the membrane to release the substance from within the cavity.

2. The device of claim 1, wherein the substance comprises medication.

3. The device of claim 1, wherein the locally heated portion of the stack of insulating layers of the membrane has a lateral dimension that is less than about two times a thickness of the membrane.

4. The device of claim 1, wherein a portion of the electrode structure comprises a V-shaped electrode, wherein an apex portion of the V-shaped electrode has a width that is less than a width of a remaining portion of the V-shaped electrode, and wherein the apex portion is configured to provide said localized heating of the locally heated portion of the stack of insulating layers of the membrane.

5. The device of claim 4, wherein the V-shaped electrode is formed with an angle of about 108 degrees to about 120 degrees.

6. The device of claim 1, further comprising a stress layer disposed on the membrane, wherein the stress layer is configured to apply a tensile stress to the membrane and cause a portion of the membrane to peel back away from a ruptured portion of the membrane.

7. The device of claim 1, wherein the stack of insulating layers of the membrane comprises at least one silicon oxide layer and at least one silicon nitride layer.

8. The device of claim 1, wherein the locally heated portion of the stack of insulating layers of the membrane further comprises a metallic material that is configured to melt due to said localized heating thereof.

9. An electromechanical device, comprising:
   a substrate comprising a cavity formed in a surface of the substrate;
   a seal disposed on the surface of the substrate surrounding an opening of the cavity;
   a membrane disposed over the surface of the substrate and covering the opening of the cavity, wherein the membrane comprises a stack of insulating layers comprising at least a first insulating layer and a second insulating layer, and wherein the seal and the membrane are configured to enclose the cavity and retain a substance within the cavity;

an electrode structure embedded within the stack of insulating layers of the membrane with the electrode structure disposed between the first and second insulating layers of the membrane;

wherein the electrode structure comprises a first contact, a second contact, and a plurality of filaments arranged adjacent to each other, wherein the plurality of filaments are electrically connected in parallel to the first contact and the second contact of the electrode structure;

wherein a surface area of a portion of the electrode structure that is disposed over the opening of the cavity is less than a surface area of the opening of the cavity; and wherein the filaments are configured to melt in succession in response to a control voltage applied to the first contact and the second contact, and cause a rupture in a portion of the stack of insulating layers of the membrane adjacent to the plurality of filaments to release the substance from within the cavity.

10. The device of claim 9, wherein the plurality of filaments include parallel filaments disposed between the first and second contacts, wherein each filament of the plurality of filaments includes a fuse portion that is configured to melt, wherein a centrally disposed filament of the plurality of filaments has a width that is greater than widths of other filaments of the plurality of filaments, and wherein the widths of the other filaments of the plurality of filaments, which are disposed on each side of the centrally disposed filament, are successively smaller.

11. The device of claim 10, wherein the fuse portions of the filaments of the plurality of filaments are arranged along a V-shaped line, wherein the fuse portion of the centrally disposed filament of the plurality of filaments is aligned to an apex of the V-shaped line.

12. An electromechanical device, comprising:
a substrate comprising a cavity formed in a surface of the substrate;
a membrane disposed over the surface of the substrate and covering an opening of the cavity, wherein the membrane comprises a stack of insulating layers comprising at least a first insulating layer and a second insulating layer, and a metallic membrane element disposed within an etched opening of at least the first insulating layer of the stack of insulting layers, wherein the metallic membrane element is aligned to the cavity;
a seal disposed between the membrane and the surface of the substrate, wherein the seal surrounds the opening of the cavity, and wherein the seal and the membrane are configured to enclose the cavity and retain a substance within the cavity; and
an electrode structure embedded within the stack of insulating layers of the membrane with the electrode structure disposed between the first and second insulating layers of the membrane and in contact with the metallic membrane element, wherein the electrode structure is configured to locally heat a portion of the metallic membrane element in response to a control voltage applied to the electrode structure, and cause at least one of melting and breaking of the locally heated portion of the metallic membrane element to release the substance from within the cavity.

13. An electromechanical device, comprising:
a substrate comprising a cavity formed in a surface of the substrate;
a membrane disposed over the surface of the substrate and covering an opening of the cavity;
a seal disposed between the membrane and the surface of the substrate, wherein the seal circumscribes the opening of the cavity, wherein the membrane is bonded to the seal, and wherein the seal and the membrane are configured to enclose the cavity and retain a substance within the cavity;
an electrode structure configured to locally heat a region in proximity to the seal in response to a control voltage applied to the electrode structure, and cause a mechanical stress that is effective to break at least a portion of the seal to release the substance from within the cavity, wherein the electrode structure is disposed on the substrate and surrounds at least a portion of a perimeter of the cavity formed in the substrate; and
a layer of polymer material disposed on the electrode structure, wherein the layer of polymer material comprises a volatile element, wherein the layer of polymer material is configured to release the volatile element in response to the heating of the polymer material by the electrode structure and cause shearing of the seal by said mechanical stress, wherein said mechanical stress comprises a shear stress that is applied to an interface connection between the seal and the membrane due at least in part to the release of the volatile element from the layer of polymer material.

14. The device of claim 13, wherein the volatile element comprises at least one of water, alcohol, and an organic material, which is released from the layer of polymer material in a gaseous form.

* * * * *